US007393828B2

(12) United States Patent
Kocer et al.

(10) Patent No.: US 7,393,828 B2
(45) Date of Patent: Jul. 1, 2008

(54) MODIFIED MSCL PROTEIN CHANNEL

(75) Inventors: Armagan Kocer, Groningen (NL);
Martin Walko, Groningen (NL);
George Thomas Robillard, Zuidhorn (NL)

(73) Assignee: Applied NanoSystems B.V., Groningen (NL)

( * ) Notice: Subject to any disclaimer, the term of this patent is extended or adjusted under 35 U.S.C. 154(b) by 6 days.

(21) Appl. No.: 11/437,873

(22) Filed: May 19, 2006

(65) Prior Publication Data

US 2006/0258587 A1    Nov. 16, 2006

Related U.S. Application Data

(63) Continuation of application No. PCT/NL2004/000812, filed on Nov. 25, 2004.

(30) Foreign Application Priority Data

Nov. 25, 2003    (EP) .................................. 03078718

(51) Int. Cl.
*A61K 47/48*    (2006.01)
*A61K 9/127*    (2006.01)
*A61P 35/00*    (2006.01)
*C07C 381/04*   (2006.01)

(52) U.S. Cl. ............................. 514/2; 514/12; 530/300; 530/324; 530/408

(58) Field of Classification Search .................... None
See application file for complete search history.

(56) References Cited

FOREIGN PATENT DOCUMENTS

WO    WO 2005/051902 A3    6/2005

OTHER PUBLICATIONS

Medical Dictionary for different channels.*
Yoshimura K, Batiza A, Kung C, Chemically Charging the Pore Constriction Opens the Mechanosensitive Channel MscL, Biophysical Journal, 2001, 80: 2198-2206.*
Moe PC, Blount P, Kung C, Functional and structural conservation in the mechanosensitive channel MscL implicates elements crucial for mechanosensation, Molecular Microbiology, 1998, 28(3): 583-592.*
Morton CC, Ion Channel Protein in Inner Ear Is Likely Long-sought Key to Hearing in FOCUS, Oct. 15, 2004.*
Benach J, Hunt JF, Shape-shifting protein channel, Nature, 2004, 427: 24-26.*
van den Berg B, Clemons WM, Collinson I, Modis Y, Hartman E, Harrison SC, Rapoport TA, X-ray structure of a protein-conducting channel, Nature, 2004, 427: 36-44.*
Channel Structure Improves Understanding of Protein Transport in Howard Hughes Medical Institute Research News, Dec. 3, 2003.*
Implications of Primary Structure in PPS96.*
Luthy R, Bowie JU, Eisenberg D, Assessment of protein models with three-dimensional profiles, Nature, 1992, 356: 83-85.*
Zhang H, Blake NW, Ouyang X, Pandolfino YA, Morgan-Capner P, Archard LC, A single amino acid substitution in the capsid protein VP1 of Coxsachievirus B3 (CVB3) alters plaque phenotype in Vero cells but not cardiovirulence in a mouse model, Archives of Virology, 1995, 140: 959-966.*
Zhang YJ, Rutledge BJ, Rollins BJ, Structure/Activity Analysis of Human Monocyte Chemoattractant Protein-1 (MCP-1) by Mutagenesis, Journal of Biological Chemistry, 1994, 269(22): 15918-15924.*
Scientists Identify a Protein Channel that Mediates the Body's Ability to Fell Frigid Temperatures, Mar. 4, 2003.*
Batiza et al., "Gating the bacterial mechanosensitive channel MscL in vivo," PNAS, Apr. 16, 2002, pp. 5643-5648, vol. 99, No. 8.
Yoshimura et al., "Chemically Charging the Pore Constriction Opens the Mechanosensitive Channel MscL," Biophysical Journal, May 2001, pp. 2198-2206, vol. 80.

* cited by examiner

*Primary Examiner*—Anish Gupta
*Assistant Examiner*—Julie Ha
(74) *Attorney, Agent, or Firm*—TraskBritt

(57) ABSTRACT

The invention relates to the field of drug delivery, in particular, to compounds and methods for the chemical modification of a proteinaceous channel to be used in pharmaceutical delivery vehicles for controlled and/or localized release of therapeutic molecules (e.g., small molecules, peptides, proteins or other macromolecules). Provided are pH- and/or light-responsive compounds capable of controlling the channel activity of a mechanosensitive channel, such as the MscL channel protein of *E. coli*, or a functional equivalent thereof, and use of these compounds to convert a mechanosensitive channel protein into a pH- and/or light-responsive channel. Also provided are drug delivery vehicles comprising a pH- and/or light-responsive channel protein.

10 Claims, 19 Drawing Sheets chargeable group

Q₁

Q₂

Q₃

R₁, R₂, R₃ = H, Me, Et, Pr, iPr, Ph, Bn

P - photocleavable chargeable group

P₁

P₂

R₁, R₂ = H, Me, Et, Pr, iPr, Ph, Bn
R₃ = H, OMe

P₃

P₄

P₅

P₆

P₇

P₈

L - linker group n = 1-10
L₁

L₂

L₃ m = 1-3
L₄

C - coupling group

C₁

C₂

C₃

C₄

C₅

C₆

X = Br, I

A)

Compound A

B)

Compound B

C)

Compound C

A

B

A)

B)

A)

B)

X= I or MscL channel protein compound F

↓ Covalent attachement to MscL
UV treatment
Low pH environments

MODIFIED MSCL PROTEIN CHANNEL

CROSS-REFERENCE TO RELATED APPLICATIONS

This application is a continuation of PCT International Patent Application No. PCT/NL2004/000812, filed on Nov. 25, 2004, designating the United States of America, and published, in English, as PCT International Publication No. WO 2005/051902 A2 on Jun. 9, 2005, which application claims priority to European Patent Application No. 03078718.8, filed Nov. 25, 2003, the contents of the entirety of each of which are hereby incorporated herein by this reference.

TECHNICAL FIELD

The invention relates to the field of biotechnology and drug delivery. The invention particularly relates to compounds and methods for the chemical modification of a proteinaceous substance, such as a channel protein, suitable for use in pharmaceutical delivery vehicles for controlled and/or localized release of therapeutic molecules (e.g., small molecules, peptides, proteins or other macromolecules).

BACKGROUND

After their discovery in 1965 (A. D. Bangham et al., *J. Mol. Biol.* 1965, 13:238-253), liposomes became a promising tool for drug delivery. Since that period, many methodologies have been developed for liposomal compositions, efficient drug encapsulation and retention, stability and targeting (M. C. Woodle and D. D. Lasic, *Biochim. Biophys. Act.* 1992, 1113:171-199). After being loaded with the desired amount of drug and being stable enough to accumulate in the target site, the next step generally is to release the content of the liposomes in response to a specific stimulus at the target. It has been hypothesized that enhanced release at the target site will significantly improve the specificity and efficacy of a liposomal drug (D. C. Drummond et al., *Pharmacol. Rev.* 1999, 51:691-744; M. B. Bally et al., *J. Liposomes Res.* 1998, 8:299-335; D. B. Penske et al., *Curr. Opin. Mol. Ther.* 2001, 3:153-158).

Various strategies have been used for triggering liposomal release at the target site. Formation of channels and defects in the liposomal bilayer, lamellar-micellar or lamellar-hexagonal phase transition, lipid phase separation and liposome fusion are some examples (P. Meers, *Adv. Drug Deliv. Rev.* 2001, 53:265-272; D. C. Drummond et al., *Prog. Lipid Res.* 2000, 39:409-460; A. Asokan and M. J. Cho, *J. Pharm. Sci.* 2002, 91:903-913; C. J. Chu and F. C. Szoka, *J. Liposome Res.* 1994, 4:361-395; J. L. Thomas and D. A. Tirrel, *Acc. Chem. Res.* 1992, 25:336-342). All these efforts have been focused on the lipid components of the liposomes, and a very limited success has been achieved (X. Guo and F. C. Szoka, *Acc. Chem. Res.* 2003, 36:335-341).

SUMMARY OF THE INVENTION

The present invention provides a set of novel compounds which, upon attachment to a proteinaceous valve (protein channel), confer a specific sensitivity to the modified protein channel, such that the channel responds to specific stimuli present at the target site (e.g., pH, light), leading to opening of the channel. A modified protein channel of the invention is advantageously used in a drug delivery vehicle (such as liposomes) to achieve a controlled and localized unloading of the contents of the vehicle at a target site, such as a tumor.

Provided is a protein that is modified with a pH-responsive compound of the general formula Q-C, wherein Q is a chargeable group selected from the chargeable groups $Q_1$, $Q_2$, and $Q_3$, and wherein C is a coupling group selected from the coupling groups $C_1$, $C_2$, $C_3$, $C_4$, $C_5$ and $C_6$ as depicted in FIG. 1. The coupling group C allows covalent attachment of the compound to a protein. Thus, a compound according to the invention may have the general formula Q-C, wherein Q is any group selected from $Q_1$-$Q_3$ and wherein C is any group selected from $C_1$-$C_6$. The chargeable group Q can be either in a charged or uncharged state, depending on the local pH environment. Also provided are proteins modified with a light-sensitive compound comprising a photocleavable chargeable group P and a coupling group C. These compounds have the general formula P—C, wherein P is any group selected from $P_1$-$P_8$ and wherein C is any group selected from $C_1$-$C_6$. Preferably, a light-sensitive compound has the formula $P_6$—$C_1$ (see, for example, Example 5). In case any one of the coupling groups $C_4$, $C_5$ and $C_6$ is used, it is, however, also possible to incorporate two Q- or P-groups, or a combination of a Q- and a P-group, in one compound. Examples of such compounds are $2(P_6)$—$C_4$, $2(Q_1)$—$C_6$, $2(P_1)$-$2(L_1)$—$C_5$ and $2(Q_1)$-$2(L_1)$—$C_5$.

A P-group can be regarded as a chargeable moiety provided with a photocleavable moiety that blocks charging of the chargeable moiety. Thus, in the absence of illumination, a compound of the invention that comprises a P-group is not chargeable. Only upon illumination of a P-containing compound, the photocleavable moiety of group P dissociates to release a chargeable moiety (see, for example, FIG. 3f). Similar to the Q-groups described above, the chargeable moiety will be protonated at a pH lower than the pKa of the chargeable moiety. Thus, the invention herewith provides pH-responsive compounds that only become pH-responsive upon illumination. The dual sensitivity of these compounds allows modification of a protein (channel) in such a manner that its activation can be tightly controlled in time.

In addition to groups Q (or P) and C, a compound may comprise a linker group L selected from the group of linker groups consisting of $L_1$-$L_4$ shown in FIG. 1. The linker group connects the chargeable group Q or the photocleavable chargeable group P to the coupling group C. The general formula of those compounds with a linker group is either Q-L-C or P-L-C. Preferably, the linker group is of the formula —$(CH_2)_n$-wherein n=1-10 (i.e., group $L_1$), more preferably $(CH_2)_2$-.

In a preferred embodiment, a modified protein is a modified proteinaceous valve, herein also referred to as a modified channel protein. A protein may also be modified with more than one compound, for example, with two or three identical compounds or with different compounds. Essentially, any type of proteinaceous substance may be modified as long as it contains at least one residue to which a coupling group C can be attached. The invention will be illustrated by the modification of a protein channel with a compound of the invention. However, other types of proteins can, of course, also be modified with a light- and/or pH-responsive compound to confer a specific sensitivity to the protein that allows for controlling the functionality of the protein with local or external stimuli (pH, light). It has been shown for some other biological systems that a charged or polar substitution in the hydrophobic pore region of gated channels, like MscL, creates easily or constitutively gating channels. For instance, the Shaker Kv channel is a channel protein gating in response to voltage changes in the membrane. Introduction of hydrophilic residues into the activation gate of Shaker Kv channels causes channel gating independent of the membrane voltage (M. Sukhareva et al., *J. Gen. Physiol.* 2003, 122:541-556).

In a preferred embodiment, the coupling group C comprises an $SSO_2CH_3$ moiety (group $C_3$ in FIG. 1) to yield a methylthiosulfonate (MTS) conjugate (see FIG. 2a). MTS conjugates react very rapidly and specifically with cysteine sulfhydryls of a protein and are, therefore, particularly suitable as a coupling group (see FIG. 2). It has been shown previously that the G22C mutant of the MscL channel protein can be activated in spheroplasts (K. Yoshimura et al., *Biophys. J.* 2001, 80:2198-2206) and growth cultures (Batiza et al., *Proc. Natl. Acad Sci. USA* 2002, 99:5643-5648) by the addition of MTS reagents. The present invention now provides pH- and also light-responsive methylthiosulfonate compounds (i.e., those comprising coupling group $C_3$), as well as pH- and light-responsive compounds with alternative coupling groups. Some pH-responsive compounds of the invention are designed to be protonated only at a pH lower than approximately 7.4 (the physiological pH of mammals including humans), whereas others have a slightly higher pKa (typically around 7.9). Compound protonation introduces a charge into the constriction part of a mechanosensitive channel (e.g., the MscL channel protein), which in turn leads to channel opening. A decreased pH can, for example, be found around solid tumors, liver cells, sites of inflammation and ischemic areas in the body.

As will be described below, of particular interest are pH-responsive compounds of the general formula $Q_1$-$L_1$-$C_3$. An example of such a compound is $R_1R_2N$—$CH_2$—$(CO)O$—$(CH_2)_2$—$S(SO_2)$—$CH_3$, wherein $R_1$ and $R_2$ are each independently H or $CH_3$, preferably wherein $R_1$ and $R_2$ are $CH_3$. FIG. 5 shows the structures of the compounds wherein $R_1$ and $R_2$ are both H (panel A; compound A: $Q_1[R_1=R_2=H]$-$L_1$[n=2]—$C_3$), wherein $R_1$ is H and $R_2$ is $CH_3$ (panel B; compound B: $Q_1[R_1=H, R_2=Me]$-$L_1$[n=2]—$C_3$) and wherein $R_1$ and $R_2$ are both $CH_3$ (panel C; compound C: $Q_1[R_1=R_2=Me]$-$L_1$[n=2]—$C_3$).

Examples of light-sensitive pH-responsive compounds of the invention can have the general formula P—C or P-L-C. It will be understood that, according to the invention, many different combinations can be made with the different photocleavable groups $P_1$-$P_8$, coupling groups $C_1$-$C_6$ and, optionally, linker groups $L_1$-$L_4$. Preferred compounds of this type include compound $P_1[R_3=OMe, R_1=H]$-$L_1$[n=1]-$C_3$ (compound D (see FIG. 6c); FIG. 6) and compound $P_2[R_3=OMe, R_1=Me]$-$L_1$[n=2]—$C_3$ (compound F; FIG. 15). Another preferred light-sensitive compound is compound $P_6$—$C_1$[X=I] (compound E) (see FIG. 12c), whose synthesis is described in Example 5 and schematically depicted in FIG. 12. A light-sensitive or pH-responsive compound of the invention is easily attached to a protein, for example, a mechanosensitive (MscL) channel protein, via the coupling group C.

Also provided herein are methods for providing a compound according to the invention that involve standard step-by-step synthesis methods, reactions and reagents well known in the field of (medicinal) organic chemistry. The synthesis of a pH-responsive compound and a light-sensitive pH-responsive compound of the invention is exemplified in Examples 1 and 5 (see also FIGS. 4, 6 and 12). The starting materials required for the synthesis are typically commercially available in high purity.

A further aspect of the invention relates to a method for providing a modified mechanosensitive channel of large conductance, preferably the MscL channel protein of *E. coli*, or a functional equivalent thereof. In nature, the channel works as a membrane tension sensor. It protects cells from lysis under hypo-osmotic shock conditions. Upon shock, water influx creates a turgor pressure in the cells and, as a result, tension in the membrane increases. The MscL channel senses the increase in the membrane tension and forms an approximately 3.5 nm non-selective pore in the membrane and releases osmolytes to protect the cell from bursting (S. I. Sukharev et al., *Annu. Rev. Physiol.* 1997, 59:633-657; C. Cruickshank et al., *Biophys. J.* 1997, 73:1925-1931). A method of the invention for providing a modified mechanosensitive channel protein, such as the MscL protein or a functional equivalent thereof, comprises the chemical modification of the channel protein with a compound of the invention by the covalent attachment of the compound via the coupling group C to a target residue of the channel protein, preferably a cysteine residue, wherein the target residue is located in a region of the channel protein that, upon introduction of a charge and/or a polar group, induces opening of the channel. Functional equivalents of the MscL channel protein of *E. coli* comprise homologues of mechanosensitive channels from other organisms. The genes encoding MscL homologues from various prokaryotes are cloned (P. C. Moe, P. Blount and C. Kung, *Mol. Microbiol.* 1998, 28:583-592). Nucleic acid and amino acid sequences are available and have been used to obtain heterologous (over)-expression of several MscL proteins (P. C. Moe et al., *J. Biol. Chem.* 2000, 40:31121-31127). A useful MscL homologue can be found in *Lactococcus lactis*. Also, mutants or otherwise chemically altered MscL proteins can be used.

A light-sensitive or pH-responsive compound, or a compound that becomes pH-responsive after photocleavage provided herein, is covalently attached to a target amino acid residue of a protein. The target residue may be naturally present or it may be artificially introduced into the protein using mutagenesis, preferably site-directed mutagenesis. Of course, the target residue of a protein to be modified by a compound of the invention is preferably located in or near a region that modulates the functionality of the protein. For example, in case of channel protein MscL, it is the region that controls the channel activity. The channel activity refers to the gating threshold, the frequency of change between the open, intermediate (if present) and the closed states and the residence time in the open/intermediate state (also known as dwell time).

One region of interest for modifying a channel protein is the region that corresponds to the first cytoplasmic domain of MscL of *E. coli*. This region constitutes the N-terminal part of the protein (residues 1 to 14) and it is proposed that there might be a supplementary gate formed by the first nine amino acids of the N terminus, which occlude the channel even when the transmembrane helices have spread apart (S. Sukharev et al., *Nature* 2001, 409:720-724; S. Sukharev et al., *Biophysical J.* 2001, 81:917-936). Another region corresponds to the first transmembrane domain, TM1 helix, of *E. coli* MscL (residues 15 to 45). This is the most conserved region (G. Chang et al., *Science* 1998, 282:2220-2226; R. H. Spencer et al., *Curr. Opin. Struct. Biol.* 1999, 9:448-454) within the MscL family.

Another region useful for modification may be the loop region (residues 46 to 75). Mutagenesis studies have implicated this region as being important in MscL gating (P. Blount et al., *Proc. Natl. Acad. Sci. USA* 1996, 93:11652-11657; J. A. Maurer et al., *J. Biol. Chem.* 2000, 275:22238-22244; Ajouz et al., *J. Biol. Chem.* 2000, 275:1015-1022; Gu et al., *Biophys. J.* 1998, 74:2889-2902). Observation of a significant number of loss-of-function mutants in this region recently led to the hypothesis that the loop serves as a spring connecting the first and the second transmembrane domains (Maurer et al., *J. Biol. Chem.* 2003, 278:21076-21082). Besides gain-of-function and loss-of-function mutations, there are also mutations in the loop region that are known to alter the channel kinetics and sensitivity. For example, mutation Gln56His led to changes in channel kinetics and tension sensitivity depending on the pH on the periplasmic but not cytoplasmic side of the membrane (Blount et al., *The EMBO J.* 1996, 15:4798-4805; P. Blount et al., *Proc. Natl. Acad. Sci. USA* 1996, 93:11652-11657). When glutamine 56 is mutated to proline, it causes changes in the gating sensitivity. Replacement of the 46th position (normally a glycine residue) with aspartic acid creates a severe gain-of-function mutant (X. Ou et al., *Proc. Natl. Acad. Sci. USA* 1998, 95:11471-11475). Yet another region of interest for modification corresponds to amino acid residues 76 to 100 of the MscL protein.

Of particular interest is the modification of a target residue in the region that corresponds to around position 23 of the MscL protein of *E. coli*. Mutagenesis experiments have shown the region located around Val 23 to be structurally and functionally very important (E. Perozo et al., *Nature* 2002, 418:942-948; X. Ou et al., *Proc. Natl. Acad. Sci. USA* 1998, 95:11471-11475; J. A. Maurer et al., *J. Biol. Chem.* 2000, 275:22238-22244). In addition, it has been shown that mutation of residue K31 can lead to changes in MscL gating (P. Blount et al., *Proc. Natl. Acad. Sci. USA* 1996, 93:11652-11657). Furthermore, mutagenesis experiments have pointed out the 22nd amino acid position in the MscL channel as one of the important sites that affect the channel gating properties and kinetics. While a hydrophobic moiety at this position makes the channel constriction more stable, a hydrophilic residue destabilizes this region and leads to channel opening without any extra energy input (K. Yoshimura et al., *Biophys. J.* 1999, 77:1960-1972). Thus, in a preferred embodiment of the invention, a protein channel is modified with a compound of the invention at the position that corresponds to residue 22 of the *E. coli* MscL protein. In case of a preferred *E. coli* MscL, the original amino acid at the 22nd position, glycine, is mutated to a cysteine in order to create a target site for the attachment of a pH-sensitive compound. Recently, Bartlett et al. identified new amino acid residues in the transmembrane domain of MscL that can be modified with MTSET, a positively charged MTS reagent, and gate the channel even in iso-osmotic conditions in intact *E. coli* cells (Bartlett et al., *PNAS* 2004, 101:10161-10165). These residues can be modified with a compound of the invention.

Combinations of different target residues for attachment of compounds that are pH-sensitive, light-sensitive or a combination of both, can also be used to control functional properties of the channel protein. Alternatively, target residues for attachment can be combined with other mutations that modify channel function. These can be located either closely together in the primary sequence or in different regions of the polypeptide, or even in different polypeptide chains of the multimeric channel protein. The invention further provides a modified mechanosensitive channel protein wherein the channel protein is modified with at least one compound of the invention. In a preferred embodiment, the modified mechanosensitive channel protein is the MscL channel protein of *E. coli*, or a functional equivalent thereof. As said, a compound can be straightforwardly attached to a desired target residue, optionally via cysteine modification, by contacting the protein with the compound under conditions that allow the formation of a covalent bond between the residue and group C of the compound, preferably followed by removal of excess compound (see Example 2). Modification of the channel protein with a compound of the invention can be used to modify the gating properties of a proteinaceous valve. More specifically, the compounds allow conversion of a channel that was previously only mechanosensitive into a pH- and/or light-responsive channel. In some cases, in addition to the pH- and/or light-responsive gating, the mechanosensitivity of the channel protein is retained. A modified channel protein according to the invention is highly attractive for use as a triggerable valve in drug delivery vehicles, for example, for controlled and/or localized release of therapeutic molecules at a target site. A modified protein channel can be reconstituted in a lipid-based delivery vehicle, such as proteoliposomes, that can subsequently be loaded with one or more therapeutic molecules. It has been found that MscL is active in lipid vehicles that consist of positively and/or neutrally charged lipids, as well as negatively and/or neutrally charged lipids. Lipid vehicles comprising the positively and/or neutrally charged lipids are more resistant to uptake by cells of the mononuclear phagocytic system. Lipid vehicles of the invention, therefore, preferably comprise positively and/or neutrally charged lipids. Such vehicles exhibit improved half-lives in the bloodstream. Such vehicles also demonstrate improved targeting to non-mononuclear phagocytic system cells. The lipid part directed towards the exterior of a lipid vehicle of the invention preferably consists predominantly of positively and/or neutrally charged lipids, thereby postponing or nearly completely avoiding cellular uptake through negatively charged lipids. Apart from increasing the half-life of the vehicle in the blood stream, different lipids can also be used to alter the amount of added pressure needed to activate the channel in the vehicle. This results from changes in the lateral pressure profile across the membrane associated with alterations in membrane composition.

In another preferred embodiment, the lipid vehicle contains neutral lipids as well as lipids with a polymer chain attached to the polar headgroup, preferably polyethyleneglycol (PEG), more preferably with a molecular weight (of the PEG chain) of approximately 2000. Although these liposomes may contain a negative charge, they have been shown to have an increased circulation time in blood (see, e.g., D. C. Drummond et al., *Pharmacol. Rev.* 1999, 51:691-744, and references therein), compared to liposomes that do not expose polymer chains on their surface. It is believed that this results from the fact that the polymer chains exclude (at least partially) other macromolecules from the exterior of the liposome, in this way reducing binding of blood plasma opsonins, and consequently, uptake by the reticuloendothelial system.

Therapeutic molecules are typically biologically active compounds or precursors thereof, such as pro-drugs that are converted in the body into an active drug. They include antineoplastic agents, microbial compounds, immunomodulators, peptides and peptidomimetics. A biologically active compound may be included in the delivery vehicle as a single active agent or in combination with other biologically active compounds.

A delivery vehicle according to the invention may also comprise targeting ligands to achieve site-specific targeting of the vehicle to a predetermined target site. Depending on the target site, various types of targeting ligands may be attached to the liposome surface, including (anti-tumor) antibodies or fragments thereof, carbohydrates and vitamins.

The application of a modified protein channel as a valve in proteoliposomes that can be triggered is nicely illustrated by a fluorescent efflux assay described in Example 3. Herewith, a method is provided for controlling the release of therapeutic molecules at a target site of a subject, comprising loading a delivery vehicle comprising a modified channel protein, such as MscL or a functional equivalent thereof, with one or more drugs, introducing the loaded delivery vehicle into the subject to allow delivery to the target site and triggering release of the drug(s) by a physiological trigger (pH below approximately 7.4), optionally following an external trigger (illumination with light). A pharmaceutical composition comprising a delivery vehicle with a modified MscL protein of the invention and a pharmaceutically acceptable carrier is also provided. A modified channel protein or a delivery vehicle comprising a channel protein is of use for the (time) controlled release of a therapeutic molecule to a target site. For instance, it is known that in tumors, the pH is very often considerably lower than in the normal tissue surrounding the tumor. Other areas in the body that have a lowered pH are the liver, areas of inflammation and ischemic areas. By using a pH-sensitive delivery vehicle of the invention, it is now possible to safely deliver an anti-cancer drug in an encapsulated form to a tumor site, where its release is subsequently triggered by the locally lowered pH, which release may be further controlled by an external light stimulus. Various anti-cancer drugs may be used, including cisplatin, carboplatin, methotrexate, 1-β-D-arabino-furanyl-cytosine (ara-C), 5-fluoro-uracil, floxuridine, and gemcitabine.

For an ideal triggered drug release system, the compound-modified protein channel molecule in the liposomes should be sensitive enough to respond to the small changes of stimuli. The pH in solid tumors and at sites of inflammation is about 0.4 to 0.8 pH unit lower than physiological pH (pH 7.3 to 7.5). We herein provide a modified channel protein that is highly pH-sensitive. When this channel protein was reconstituted in proteoliposomes, a decrease of only 0.2 pH units resulted in up to 30% more channel activity. This pH range of activity is also compatible with physiological conditions.

In addition to the sensitivity, the response time to the trigger may also be important. For instance, in endosome-targeted delivery, the liposomes should respond to the pH of endosomes within 10 to 30 minutes before going to the lysosomal degradation route. The modified channel proteins according to the invention respond to pH changes almost immediately. Incorporation of a photocleavable group in a compound of the invention provides a control mechanism over the response time of the compound such that it can be decided when to activate the compounds by removal of the photolysable group. The modified channel proteins of the invention do not negatively affect the integrity and stability of the drug delivery vehicle.

DETAILED DESCRIPTION OF THE INVENTION

Examples

Example 1

Synthesis of pH- and Light-Responsive Compounds

Methylthiosulfonate (MTS) derivatives react very rapidly and specifically with cysteine sulphydryls and introduce the functional group into the protein. The sulfinic acid by-product of the reaction decomposes rapidly to low-molecular-weight volatile products, which do not, in general, affect the stability of the disulfide bond formed or the activity of the enzyme. This example shows the synthesis of both pH- and light-sensitive MTS-based compounds.

A. General Synthesis of the pH-Responsive Compounds

Material and Methods

Figure 1:
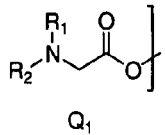
FIG. 1. The compounds of the invention are composed of different groups. Compounds comprise a coupling group C in combination with either a chargeable group Q or (in case of the light-sensitive compounds) with a photocleavable chargeable group P. Photocleavage of group P leads to unmasking of a chargeable moiety. The chargeable group Q or chargeable moiety of group P released upon illumination can either be in a charged or uncharged state, depending on the environment or external stimuli, and will be directly responsible for alternation of the protein properties. The coupling group C can bind to a cysteine residue of the protein, thereby attaching the compound to the channel protein. The Q- or P-group may be connected to a C-group through a linker L. The Q-groups are designed to achieve a suitable pKa of the charged group. Me=methyl; Et=ethyl; Pr=propyl; iPr=isopropyl; Ph=phenyl; Bn=benzyl.
Figure 1:
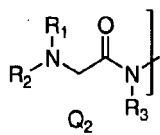
Figure 1:
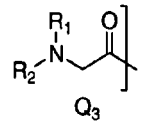
Figure 1:
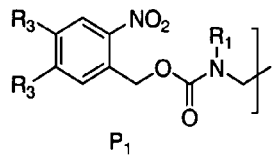
Figure 1:
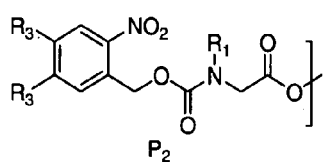
Figure 1:
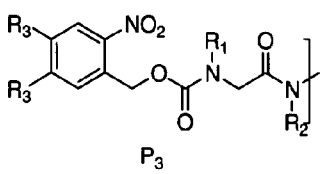
Figure 1:
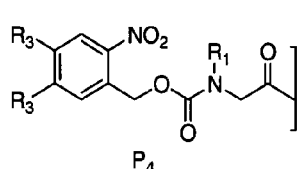
Figure 1:
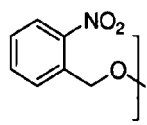
Figure 1:
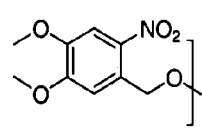
Figure 1:
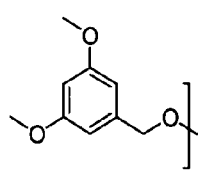
Figure 1:
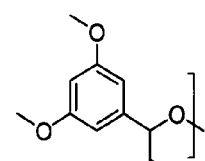
Figure 1:
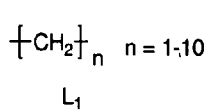
Figure 1:
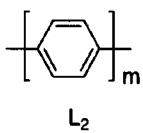
Figure 1:
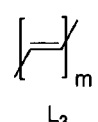
Figure 1:
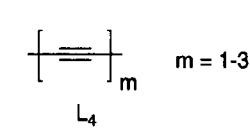
Figure 1:
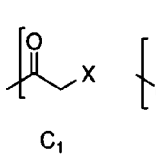
Figure 1:
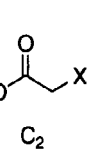
Figure 1:
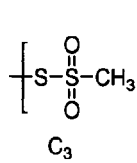
Figure 1:
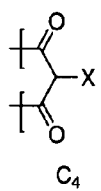
Figure 1:
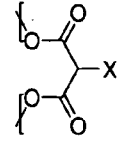
Figure 1:
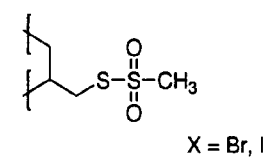
Figure 2:
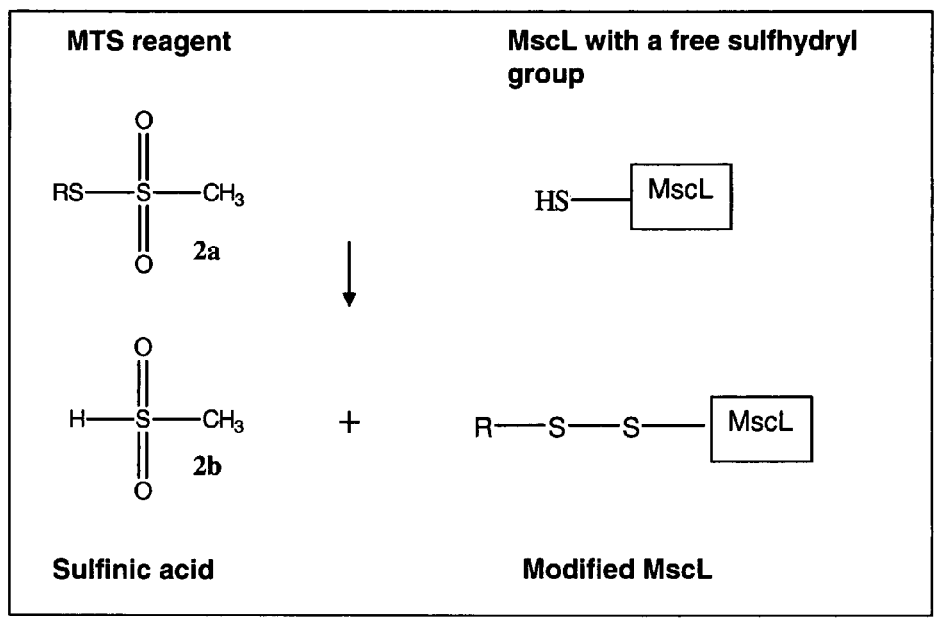
FIG. 2. The general chemical modification mechanism of a cysteine sulfhydryl of a protein (e.g., MscL channel protein) with methylthiosulfonate (MTS)-based compounds (see FIG. 2a), i.e., those comprising $C_3$ as a coupling group. Methylthiosulfonate reacts very rapidly and specifically with cysteine sulfhydryls and attaches the compound to the protein. The sulfinic acid by-product of the reaction (see FIG. 2b) decomposes rapidly to low-molecular-weight volatile products, which do not, in general, affect the stability of the disulfide bond formed or the activity of the channel protein.
Figure 3:
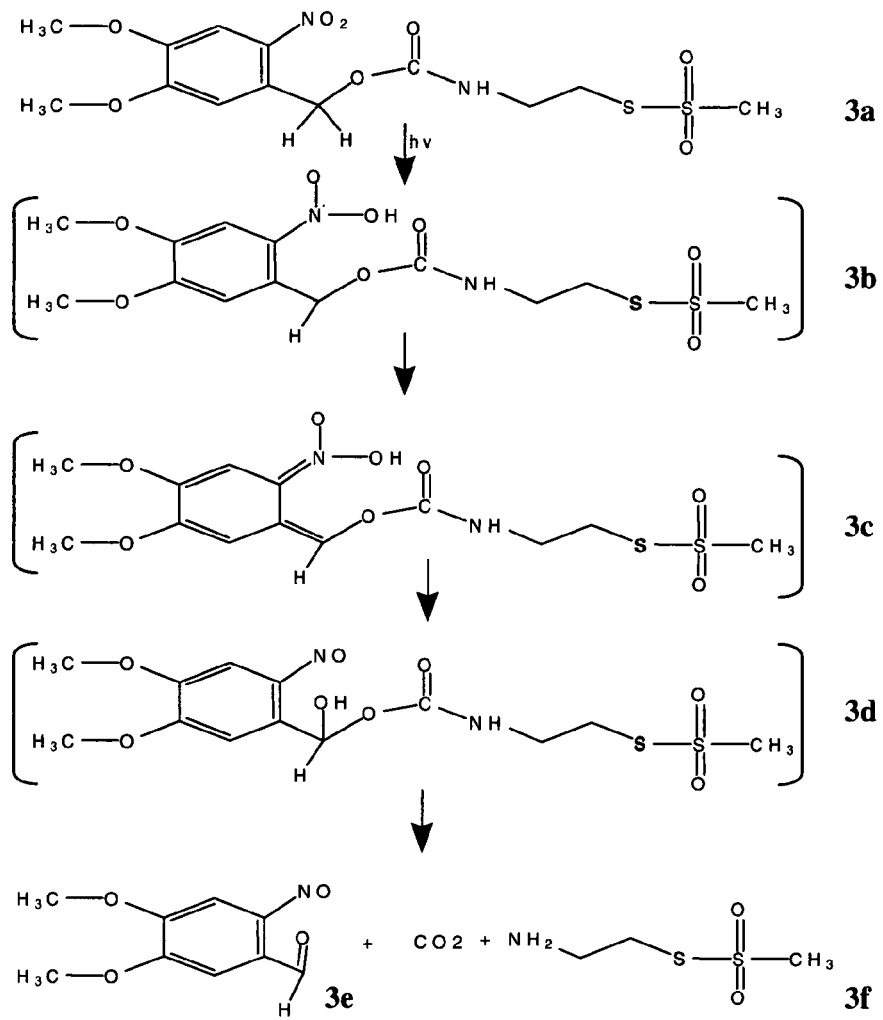
FIG. 3. The photocleavage reaction of compound D: $P_1[R_3=OMe, R_1=H]-L_1[n=1]—C_3$.
Figure 4:
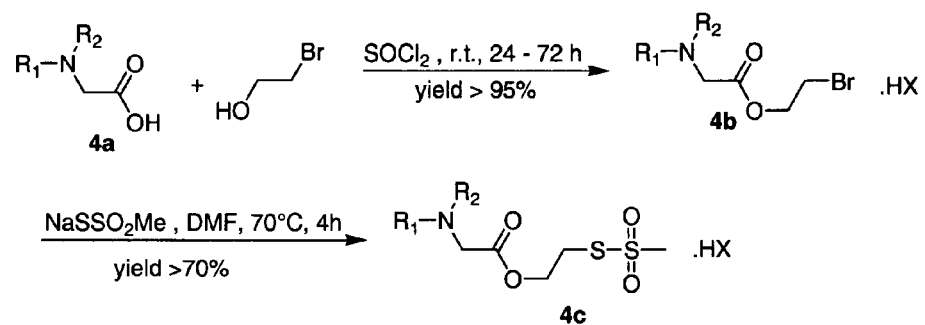
FIG. 4. Schematic presentation of the synthesis of a pH-responsive compound, wherein the coupling group is based on MTS (compound $Q_1$-$L_1$-$C_3$). 4a: Glycine or its N-alkylated derivative; 4b: 2-bromo-ethyl ester of glycine or its N-alkylated derivative 4c: 2-methanesulfonylsulfanyl-ethyl ester of glycine or its N-alkylated derivative.

The schematic presentation of the compound synthesis is given in FIG. 4. In the first reaction, glycine or its N-alkylated derivative (see FIG. 4a) in the form of the free compound or as a HCl salt (20 mmol), was suspended in 2-bromoethanol (14.3 ml, 200 mmol) and cooled to 0° C. Thionyl chloride (1.8 ml, 25 mmol) was added dropwise and reaction mixture was stirred at room temperature until a clear solution was obtained. Resulting solution was poured into 200 ml of ether, precipitated solid was filtered, washed with ether and dried in vacuo. In the case that only oil separates instead of precipitate, ether was decanted; oil was washed with ether (2×100 ml) and all the residual solvents were removed in vacuo. Oil usually solidifies upon standing overnight at 40° C. Compound bromo-ethyl ester of glycine or its N-alkylated derivative (see FIG. 4b), was obtained as HCl salt.

In the second reaction, the salt of 2-bromo-ethyl ester of glycine or its N-alkylated derivative (see FIG. 4b) (10 mmol) was dissolved in DMF (10 ml) and sodium methanethiosulfonate (1.47 g, 11 mmol) was added. Mixture was heated at 70° C. for four hours, solid precipitate was filtered out and DMF was evaporated in vacuo. The residue was dissolved in a small amount of boiling acetonitrile (20 ml), filtered, and filtrate evaporated in vacuo. Product, 2-methanesulfonylsulfanyl-ethyl ester of glycine or its N-alkylated derivative (see FIG. 4c), is also obtained as HCl salt. Solid products can be recrystallized from acetonitrile-ether or ethanol-ether.

The yield of the first synthesis reaction was over 95%, and the purity of the compound, 2-bromo-ethyl ester of glycine or its N-alkylated derivative (see FIG. 4b), was over 98%. The yield of the second reaction was 70 to 90%. The resulting compound, 2-methanesulfonylsulfanyl-ethyl ester of glycine or its N-alkylated derivative (see FIG. 4c), may contain a small amount (<5%) of NaCl.

Figure 5:
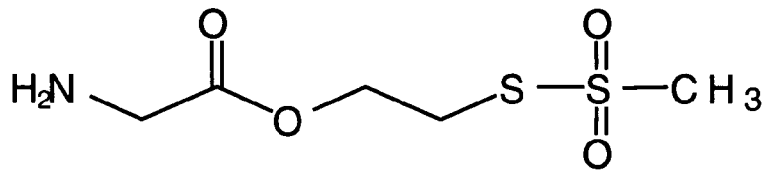
FIG. 5. Examples of pH-sensitive compounds of the formula $Q_1$-$L_1$-$C_3$. A) $R_1$ and $R_2$ are both H (compound A: $Q_1[R_1=R_2=H]-L_1[n=2]-C_3$). B) $R_1$ is H and $R_2$ is $CH_3$ (compound B: $Q_1[R_1=H, R_2=Me]-L_1[n=2]—C_3$). C) Both $R_1$ and $R_2$ are $CH_3$ (compound C: $Q_1[R_1=R_2=Me]-L_1[n=2]—C_3$).
Figure 5:
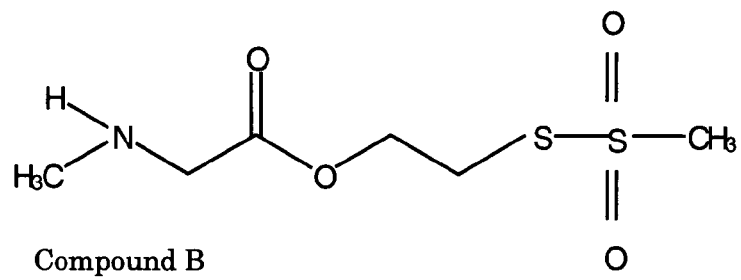
Figure 5:
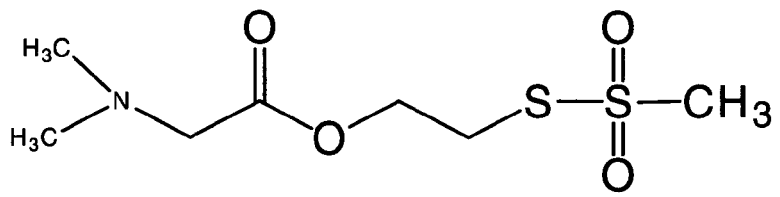

1. The first pH-responsive compound obtained by a starting compound in which both two functional groups ($R_1$ and $R_2$) of the glycine or its N-alkylated derivative (see FIG. 4a) were hydrogen. The synthesized molecule (compound A: $Q_1$[$R_1$=$R_2$=H]-$L_1$[n+2]—$C_3$) is shown in FIG. 5A.

2. The second pH compound obtained by a starting compound in which the functional groups ($R_1$ and $R_2$) of the glycine or its N-alkylated derivative (see FIG. 4a) were a hydrogen and a methyl, respectively. The synthesized molecule (compound B: $Q_1$[$R_1$=H, $R_2$=Me]-$L_1$[n=2]—$C_3$) is shown in FIG. 5B.

3. The third pH compound obtained by a starting compound in which both functional groups ($R_1$ and $R_2$) of the glycine or its N-alkylated derivative (see FIG. 4a) were methyls. The synthesized molecule (compound C: $Q_1$[$R_1$=$R_2$=Me]-$L_1$[n=2]—$C_3$) is shown in FIG. 5C.

B. General Synthesis of Light-Sensitive pH-Responsive Compounds

Material and Methods

Figure 6:
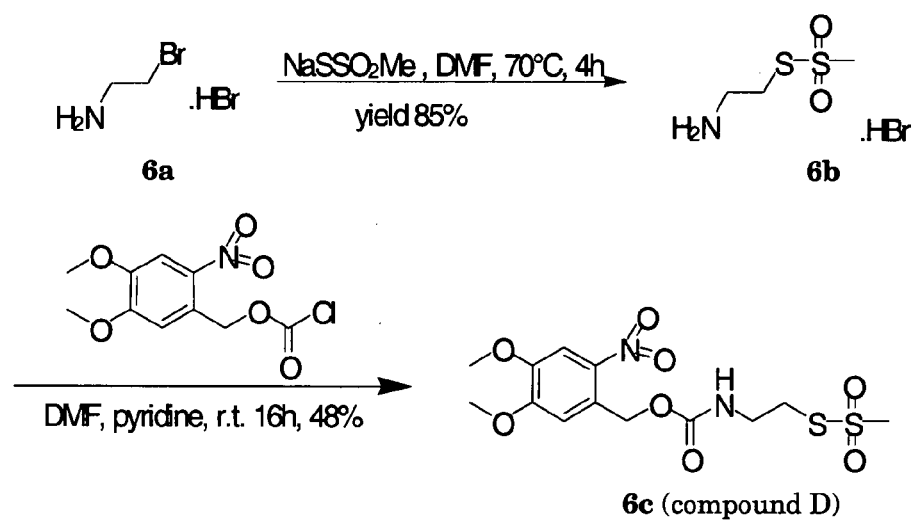
FIG. 6. Schematic presentation of the synthesis of a light-sensitive pH-responsive compound of the formula $P_1[R_3=OMe, R_1=H]-L_1[n=1]—C_3$ (see FIG. 6c. 6a: 2-bromoethylamine hydrobromide 6b: Methanethiosulfonic acid S-(2-amino-ethyl) ester hydrobromide; 6c: Methanethiosulfonic acid S-[2-(4,5-dimethoxy-2-nitrobenzyloxycarbonyl-amino)-ethyl] ester.

The schematic presentation of the synthesis of light-sensitive compounds is given in FIG. 6. In the first reaction, sodium methanethiosulfonate (1.47 g, 11 mmol) was added to the solution of 2-bromoethylamine hydrobromide (see FIG. 6a) (2.05 g, 10 mmol) in DMF (5 ml) and mixture was heated at 70° C. for four hours, solid precipitate was filtered out, and DMF was evaporated in vacuo. The residue was dissolved in a small amount of boiling acetonitrile (20 ml), filtered, and the filtrate evaporated in vacuo. The recrystallization from acetonitrile-ether gave product.

In the second reaction, 236 mg, 1 mmol of methanethiosulfonic acid S-(2-amino-ethyl) ester hydrobromide (see FIG. 6b) was dissolved in 3 ml of DMF and 6-nitroveratryl-chlorofotmate (303 mg, 1.1 mmol) and pyridine (0.5 ml) were added. After overnight stirring, the mixture was poured into water (10 ml) and extracted with dichloromethane (3×30 ml). All the solvents were evaporated in vacuo and product, methanethiosulfonic acid S-[2-(4,5-dimethoxy-2-nitro-benzyloxycarbonylamino)-ethyl] ester (see FIG. 6c); compound D: $P_1$[$R_3$=OMe, $R_1$=H]-$L_1$[n=1]—$C_3$), chromatographed on Si-gel using dichloromethane as an eluent.

Results and Discussion

The yield of the first reaction was 85%, that of the second reaction was 48%. The product (see FIG. 6c); compound D: $P_1$[$R_3$=OMe, $R_1$=H]-$L_1$[n=1]—$C_3$) was soluble in DMF and DMSO, was a little soluble in dichloromethane and chloroform and was very badly soluble in other common solvents.

Example 2

Chemical Modification of the MscL Channel Protein

All synthesized compounds were attached to the MscL protein from *E. coli* via cysteine modification. In this example, the 22nd position of the protein was mutated to a cysteine.

Material and Methods

A membrane pellet fraction was obtained from a fermentor culture of *E. coli* pB104 cells containing the plasmid PB104 carrying the MscL(G22C)-6His construct. MscL was isolated to near homogeneity via a single nickel-nitriloacetic acid (Ni-NTA) metal-affinity chromatography step.

One volume of isolated detergent-solubilized MscL (0.3 mg/ml) was incubated with 0.5 volume of 160 mM compound (A-C) for 15 minutes at room temperature. The protein modification reaction was stopped and the excess label was removed by applying the sample into a gel filtration column. The protein concentration of elution fractions was determined by Bradford Assay.

The modified protein was reconstituted in synthetic lipid membranes in order to follow the channel activity. For this purpose, DOPC:Cholesterol:DSPE-PEG (70:20:10 Molar ratio) liposomes were titrated with Triton-X100 until saturation. Titrated liposomes were mixed with modified protein in 1:120 (wt:wt) protein to lipid ratio. Biobeads were used to remove the detergent. A self-quenching dye, calcein, was added and included into the interior of the proteoliposomes during reconstitution.

Results and Discussion

Five to eight grams wet weight membrane pellet was obtained from a 10 liter fermentor culture of *E. coli* PB104 cells. Approximately 3 mg protein/l of fermentor culture was isolated to near homogeneity via a single metal-affinity chromatography step. The isolated detergent-soluble protein was stable for at least six months at −80° C. The efficiency of protein modification with the compound was monitored by both a calcein assay and by mass spectroscopy.

Example 3

Functionality of a Modified MscL Channel Protein

Proteoliposomes containing modified MscL protein were analyzed by a fluorescent dye efflux assay. The activity of the channel was measured as an increase in the fluorescence of a reporter molecule, the dye calcein. Calcein is included in the liposome interior at a self-quenching concentration, but when the calcein escapes into the exterior medium, the dilution is such that quenching is completely abolished.

Materials and Methods

Figure 7A:
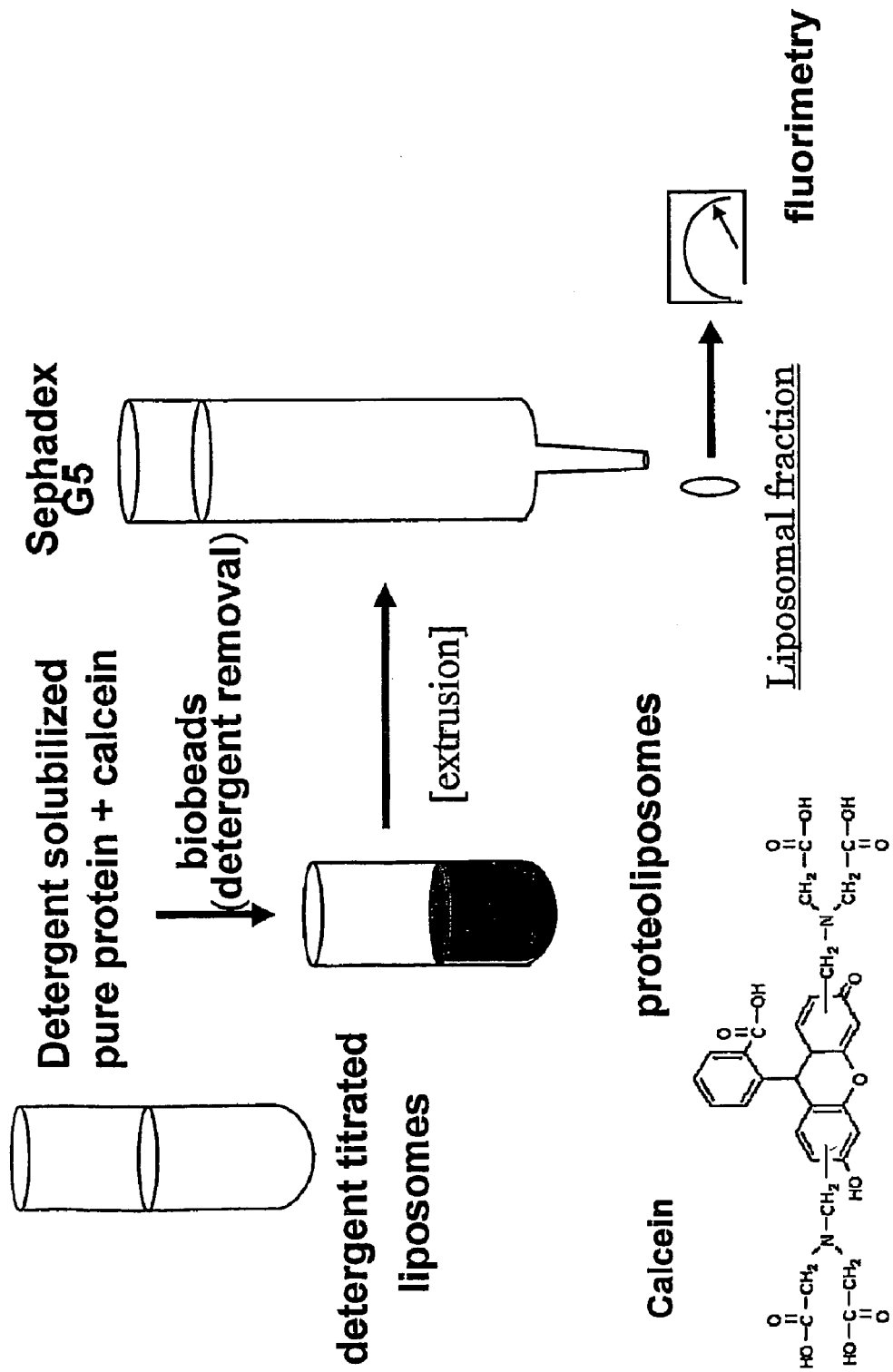
FIG. 7. Calcein Efflux Assay A) Calcein-containing proteoliposomes were prepared and liposomal fraction was separated from the free calcein by a Sephadex G50 size exclusion column; B) The schematic presentation of the efflux; C) An example of an activity measurement in the efflux assay. Arrow indicates the time when the trigger is applied. (In this particular case, the trigger is the application of 0.8 mM final concentration of [2-(Trimethylammonium)-ethyl]-methanethiosulfonate bromide (MTSET) into the measurement cuvette containing proteoliposomes.)

The schematic presentation of the efflux assay is given in FIG. 7. During reconstitution of the protein into the mixture of synthetic lipids in the presence of a detergent, a self-quenching dye, calcein, is also added into the mixture to a final concentration of 50 mM. After the reconstitution is completed by the removal of the detergent, the calcein-containing liposomal fraction was separated from the unencapsulated free calcein by passing the sample through a Sephadex G50 size exclusion column (FIG. 7A).

Figure 7B:
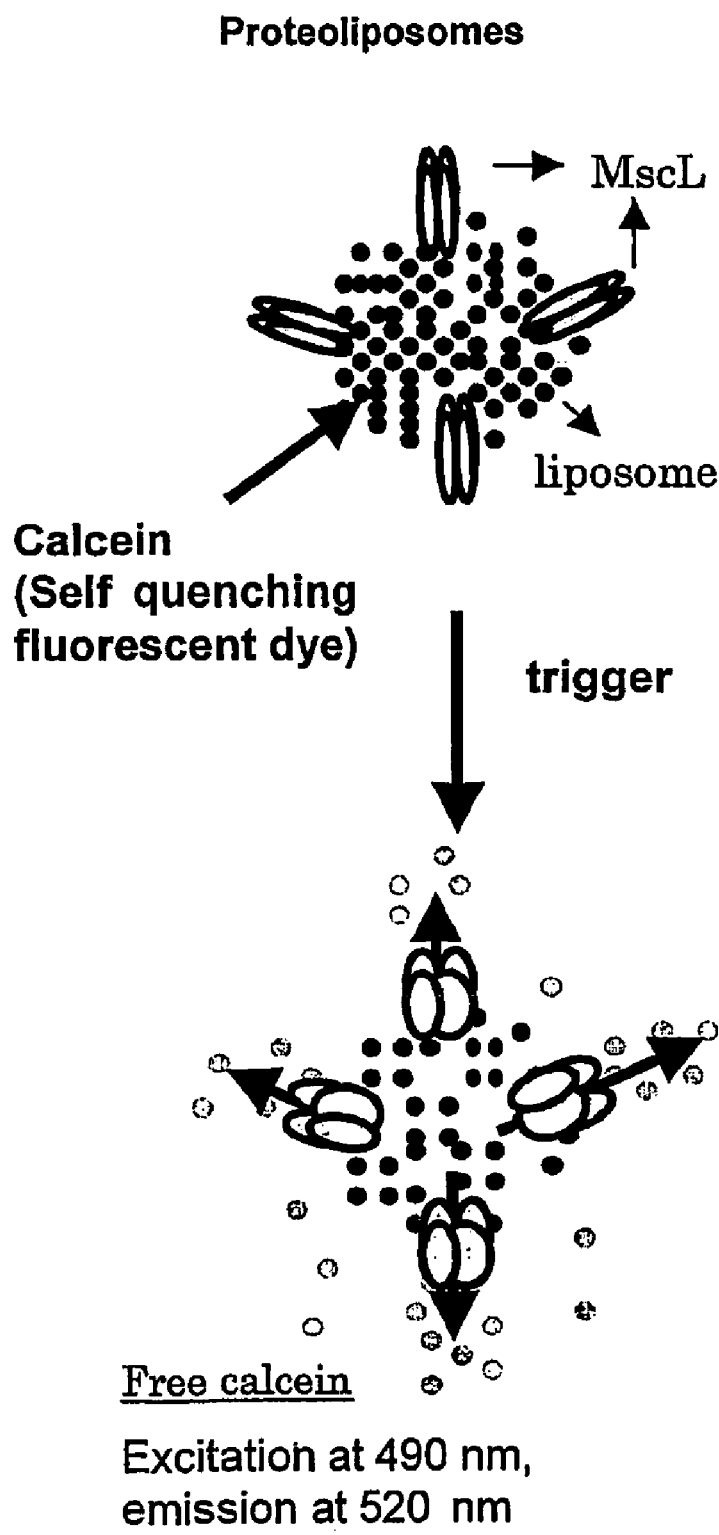
Figure 7C:
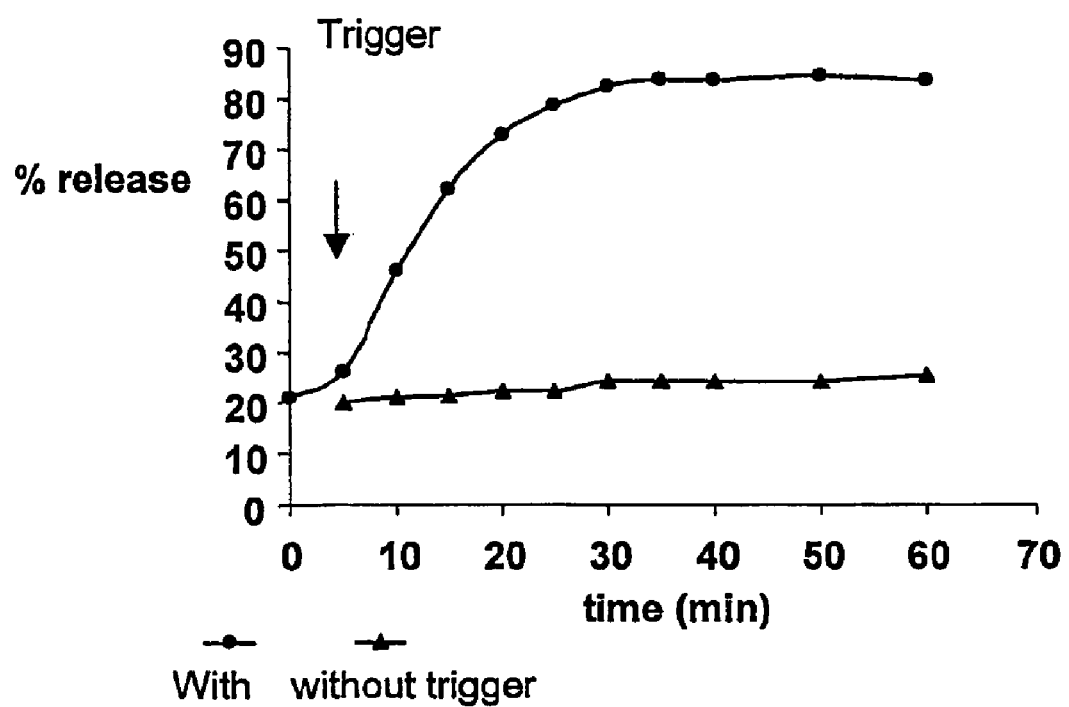

A portion of the liposomal fraction is placed in 2 ml iso-osmotic buffer and the activity of the channels is followed by measuring the increase in fluorescence as calcein becomes dequenched upon being released through the channel protein in response to a stimulus (FIG. 7B). Fluorescence was monitored with a SLM 500 spectrofluorometer Excitation and emission wavelengths were 490 (slit 2 nm) and 520 nm (slit 4 nm), respectively. A positively charged MTS reagent (MTSET) was used as a positive control. Since MTSET always carries a positive charge, it always opens the channel after it has reacted with MscL at the free sulfhydryl residue at the 22nd position (FIG. 7C).

Results and Discussion

The calcein efflux assay gives an opportunity of following the activity of MscL channels in model drug-containing proteoliposome ensembles in response to an applied stimulus. The system works fast and gives reproducible results.

Example 4

A. Channel Activity of the Protein Modified with a pH-Responsive Compound

The MscL protein was modified with the different pH-responsive compounds. The activity of the channel in response to pH was analyzed by the calcein efflux assay. In order to do that, the same buffer at different pHs were prepared and the same sample is analyzed in each buffer.

1. Compound A: $Q_1[R_1=R_2=H]-L_1[n=2]-C_3$

Figure 8:
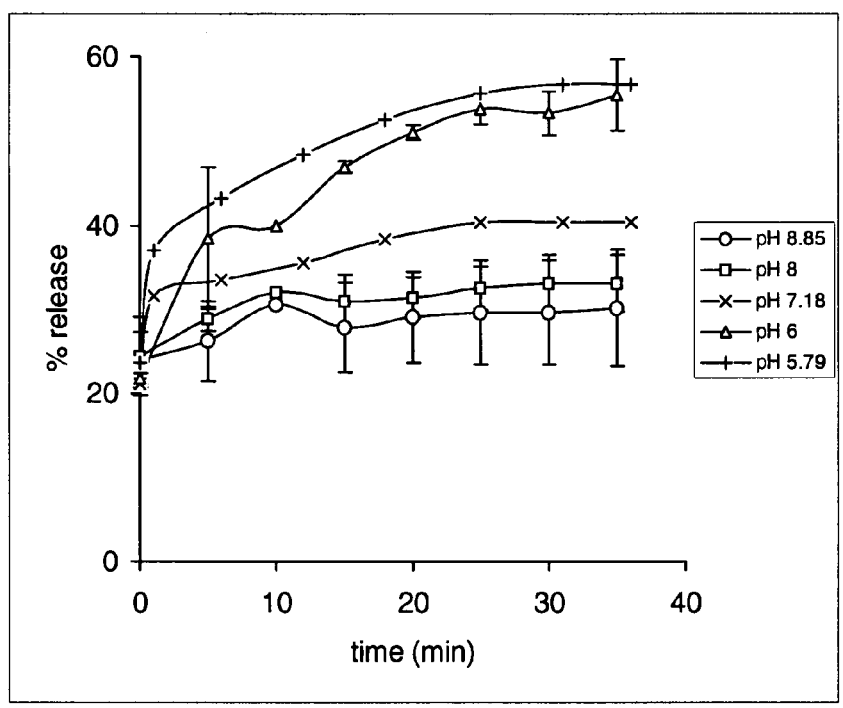
FIG. 8. Calcein efflux assay using proteoliposomes containing the MscL channel protein modified with the pH-responsive compound A ($Q_1[R_1=R_2=H]-L_1[n=2]—C_3$). The efflux assay was performed at different pHs. A) Channel activity at different pHs; B) the maximum percent fluorescence is shown as a function of pH.
Figure 8:
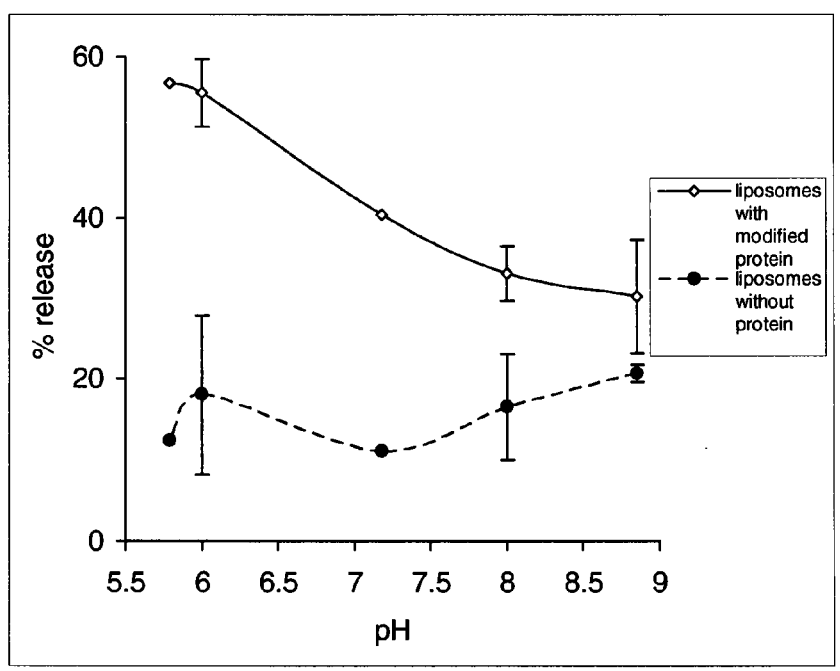

The first pH compound has $-CO(O)-CH_2NH_2(Q_1[R_1=R_2=H])$ as a chargeable group Q. The activity of proteins modified with compound A $(Q_1[R_1=R_2=H]-L_1[n=2]-C_3)$ is shown in FIG. 8. The modified protein showed a pH-dependent activation, especially at lower pHs, although there was some activity at physiological pH.

2. Compound B: $Q_1[R_1=H, R_2=Me]-L_1[n=2]-C_3$

Figure 9:
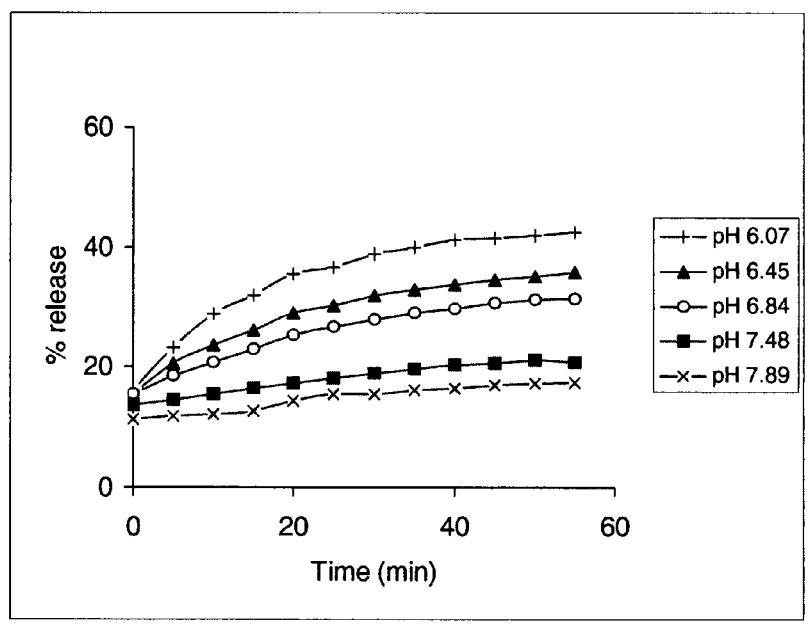
FIG. 9. Calcein efflux assay using proteoliposomes containing the MscL channel protein modified with the pH-responsive compound B ($Q_1[R_1=H, R_2=Me]-L_1[n=2]—C_3$). The efflux assay was performed at different pHs. A) Channel activity at different pHs; B) the net percent fluorescence is shown as a function of pH.
Figure 9:
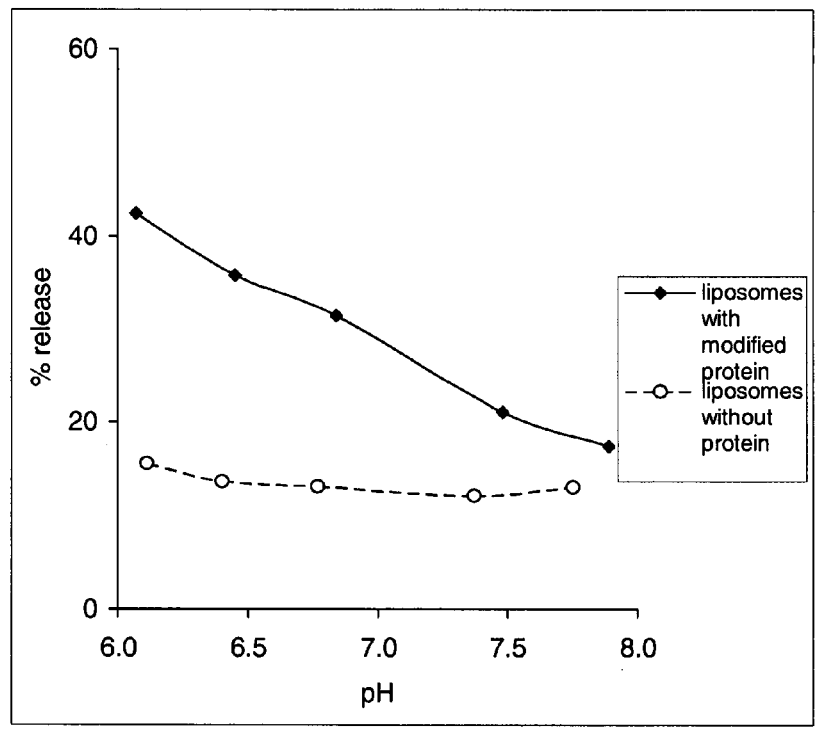

The second pH compound has $-CO(O)-CH_2NHCH_3$ $(Q_1[R_1=H, R_2=Me])$ as a chargeable group Q. The activity of proteins modified with compound B $(Q_1[R_1=H, R_2=Me]-L_1[n=2]-C_3)$ is shown in FIG. 9. The modified protein showed a pH-dependent activation. Its pKa is approximately 8. This particular compound started to show channel activity below pH 8.

3. Compound C: $(Q_1[R_1=R_2=Me]-L_1[n=2]-C_3)$

Figure 10:
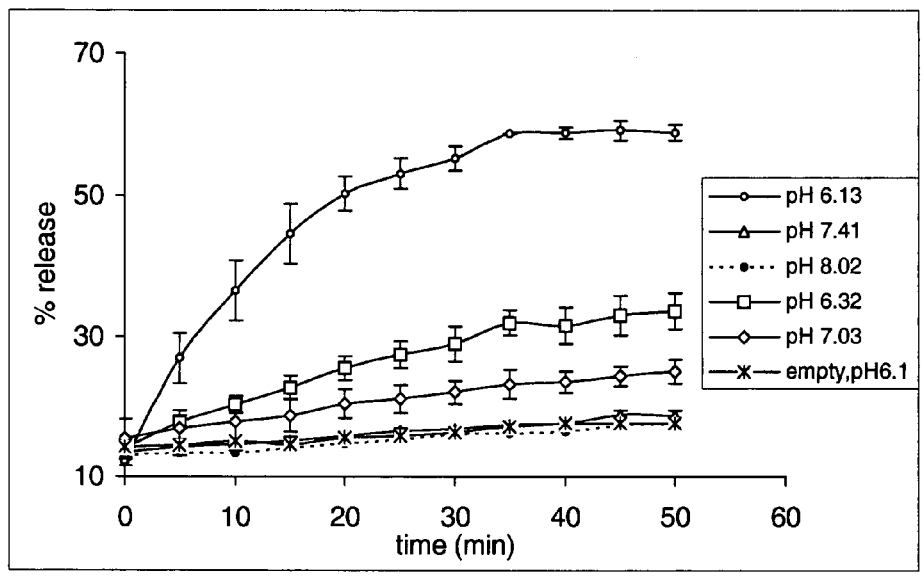
FIG. 10. Calcein efflux assay using proteoliposomes containing the MscL channel protein modified with the pH-responsive compound C ($Q_1[R_1=R_2=Me]-L_1[n=2]—C_3$). The efflux assay was performed at different pHs. A) Channel activity at different pHs; B) the maximum percent fluorescence is shown as a function of pH.
Figure 10:
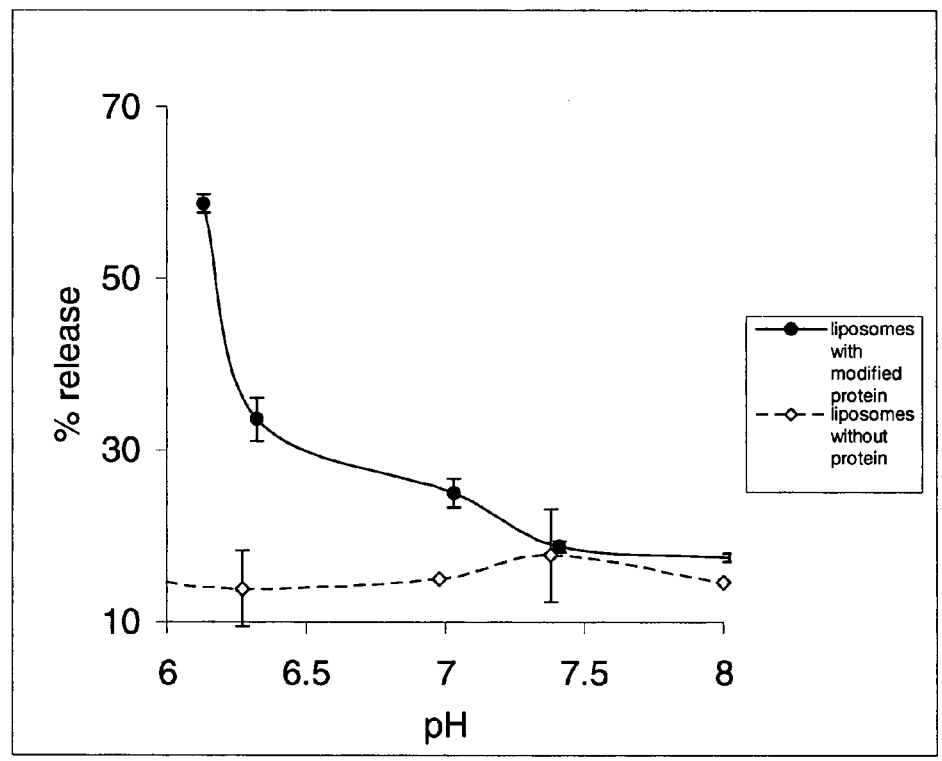

The third pH compound has $-CO(O)-CH_2N(CH_3)_2(Q_1[R_1=R_2=Me])$ as a chargeable group Q. The activity of proteins modified with compound C $(Q_1[R_1=R_2=Me]-L_1[n=2]-C_3)$ is shown in FIG. 10. The modified protein had no activity at pH 7.5, and started to be active at around pH 7.03. This is an ideal compound for the drug delivery to a target site at which the pH is lower than physiological pH. The modified channel will stay close at the normal body pH of 7.4 but will be activated (opened) at the low pH of the target site.

B. Channel Activity of the Protein Modified with a Light-Sensitive Compound.

Figure 11:
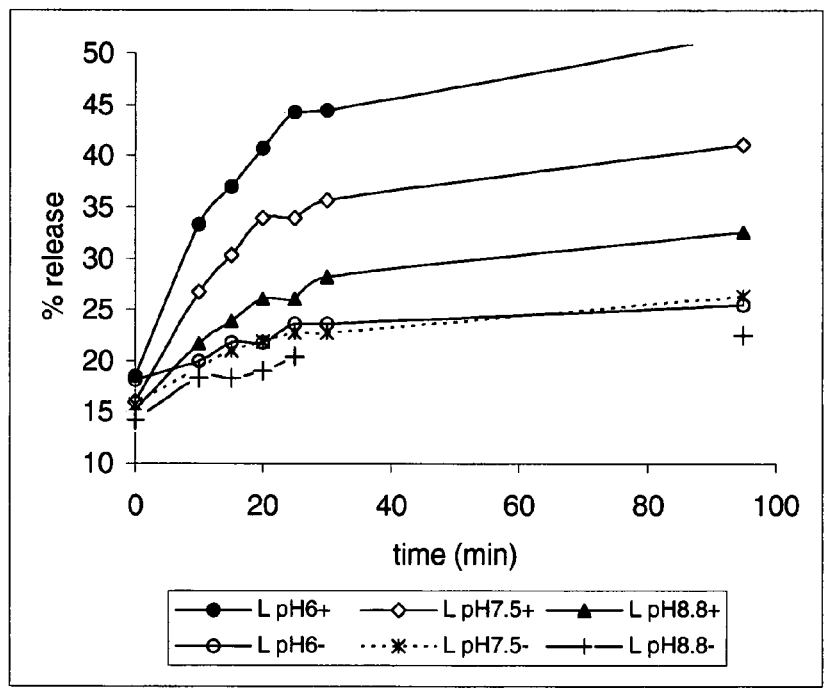
FIG. 11. Calcein efflux assay using proteoliposomes containing the MscL channel protein modified with the light-sensitive pH-responsive compound D (see FIG. 6c) ($P_1[R_3=OMe, R_1=H]-L_1[n=1]—C_3$). Calcein efflux assay of liposomes containing the modified protein is performed at different pHs. A) Channel activity at different pHs after initial illumination (+) or no illumination (−); B) The maximum percent fluorescence is shown as a function of pH.
Figure 11:
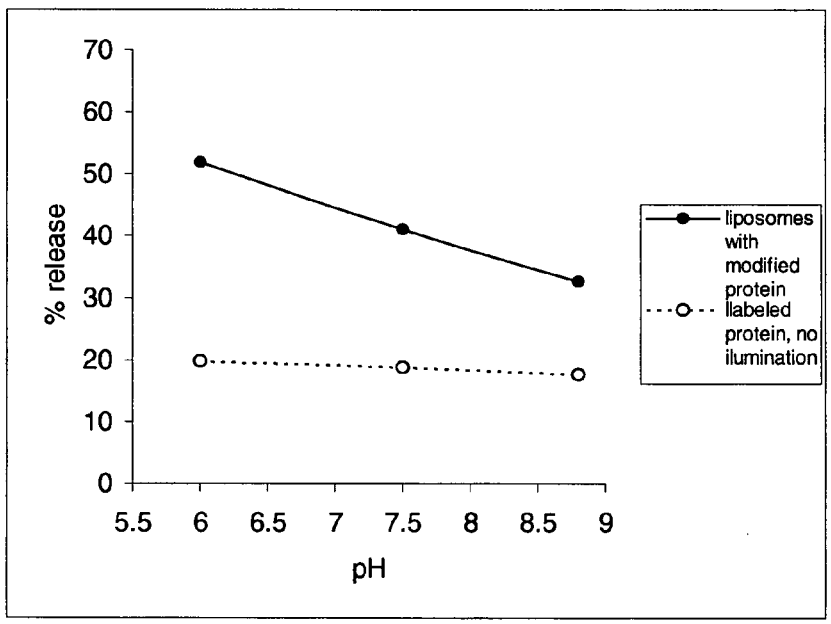

The MscL protein was modified with a light-sensitive compound. The activity of the channel was analyzed in response to pH. After measuring the initial fluorescence value for samples at each pH, they were exposed to 366 nm light for five to ten minutes. Then, the measurement was continued as before. Results are given in FIG. 11. The compound stayed inactive until the photolysis occurs. After the cleavage of the light-sensitive part by illumination, the chargeable group left behind showed a pH-dependent activity. The light sensitivity can be used both as a separate control tool to open the channel and also as a masking group to protect the chargeable group until the time a response (i.e., release) is desired.

Example 5

Chemical Synthesis of a Light-Responsive Compound

Figure 12:
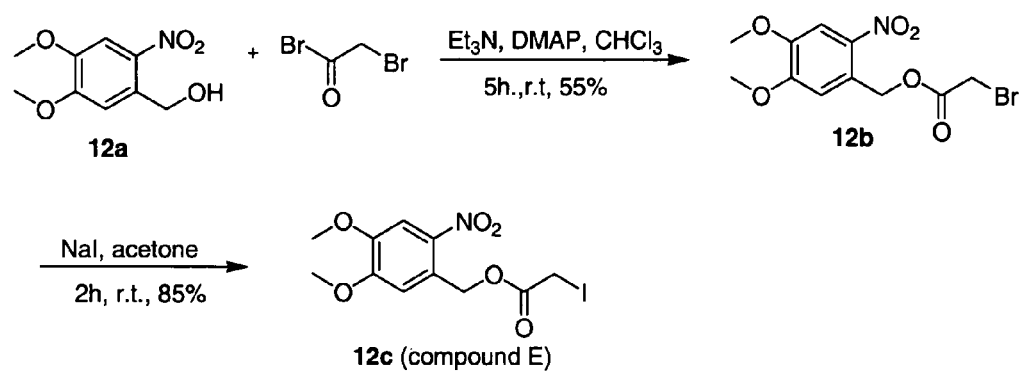
FIG. 12. Chemical synthesis of light-responsive compound $P_6$-$C_1$[X=I] (compound E) (See FIG. 12c).

This example shows the synthesis of a light-responsive compound (compound E (see FIG. 12c): $P_6$-$C_1$[X=I]) as shown in FIG. 12.

A. 5-dimethoxy-2-nitrobenzyl 2-bromoacetate

Bromoacetylbromide (0.19 ml, 2.2 mmol) was slowly added to the solution of 6-nitroveratrylalcohol (0.43 g, 2 mmol), $Et_3N$ (0.56 ml, 4 mmol) and DMAP (24 mg, 0.2 mmol) in $CHCl_3$ (5 ml). After stirring at room temperature for five hours, $CH_2Cl_2$ (20 ml) was added and the mixture was washed with HCl (1 M, 2×10 ml), $NaHCO_3$ (sat., 10 ml) and water (10 ml). Organic phase was dried over $Na_2SO_4$, evaporated and purified by chromatography (Si-gel, $CH_2Cl_2$) to yield 4.5-dimethoxy-2-nitrobenzyl 2-bromoacetate (368 mg, 55%).

B. 4.5-dimethoxy-2-nitrobenzyl 2-iodoacetate

A 4.5-dimethoxy-2-nitrobenzyl 2-bromoacetate (100 mg, 0.3 mmol) was dissolved in acetone (2 ml) and NaI (50 mg, 0.33 mmol) was added. After stirring for two hours at room temperature, mixture was filtered, evaporated and purified by chromatography (Si-gel, $CH_2Cl_2$) to yield 4.5-dimethoxy-2-nitrobenzyl 2-iodoacetate (compound E (see FIG. 12c): $P_6$—$C_1$[X=I]) (97 mg, 85%).

Example 6

Single Molecule Level Analyses of MscL Channel Proteins Modified with a pH-Responsive Compound The activity of the chemically modified MscL is analyzed real time at the single molecule level with patch clamp, a classical electrophysiological technique. This technique allows sealing a patch of membrane, which has embedded channel proteins in it, into the tip of a glass micropipette, and monitoring the ionic current flowing through the open channels in response to different conditions.

As a mechanosensitive channel, unmodified MscL needs a significant amount of tension on the membrane to gate. In patch clamp conditions, it corresponds to the application of negative pressure almost as high as that causing rupturing of the patched membrane. On the other hand, the presence of charge in the pore region of the protein reduces this need significantly, and channel protein starts to gate even without any tension.

This example shows the patch clamping of modified channel proteins at different pHs, with or without applied negative pressure. The channel activity was measured by following its conductance.

Materials and Methods

The protein from cysteine mutant MscL (cysteine in its 22nd amino acid position) was isolated, modified and reconstituted as explained in Example 2. After reconstitution, giant proteoliposomes were prepared as indicated (A. H. Delcour, B. Martinac, F. R. Blattner, C. Kung, *Biophys. J.* 1989, 56:631-636). Ten μl rehydrated lipids were placed in 100 μl bath solution and resulting giant liposomes were patched by using glass pipettes with 1 μm tip size. They were made from 100 μl borosilicate capillaries in Sutter 97/IVF micropipette puller. Single channel recordings were performed at +20 mV in symmetrical buffer conditions in 200 mM KCl, 100 mM $MgCl_2$, 5 mM HEPES, pH 6-8. Data were amplified and filtered in Axopatch1D amplifier and sampled in Digidata 1322A digitizer. Recordings were analyzed with pCLAMP8 software.

A. Compound B: $Q_1[R_1=H, R_2=Me]$-$L_1[n=2]$—$C_3$

Figure 13:
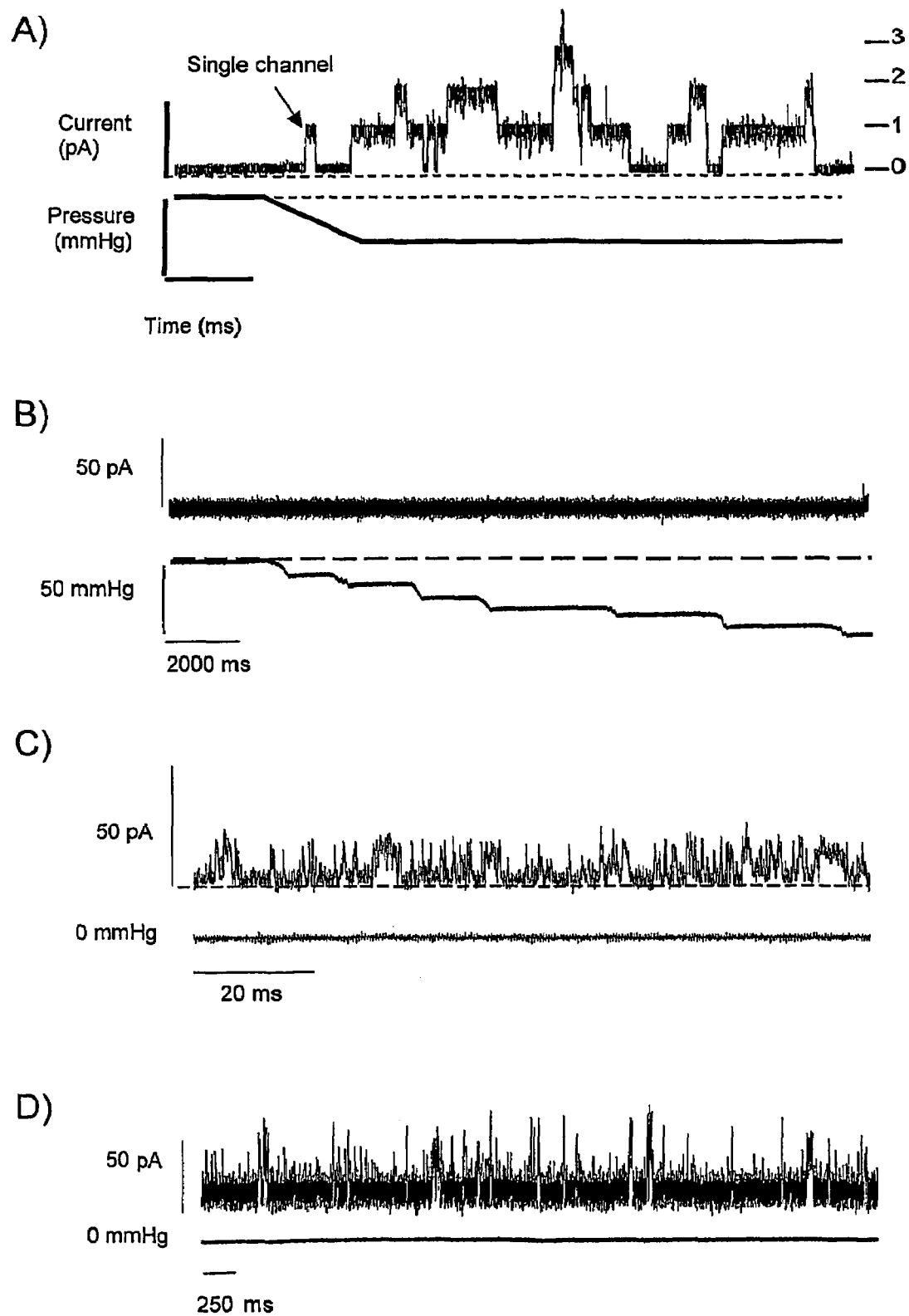
FIG. 13. Patch Clamp analysis of pH-responsive compounds. In all the cases, the upper trace shows the current and the lower one shows the negative pressure. The dashed lines indicate the value "0" for the particular signal. The channel openings are seen as boxes or spikes in the current signal. The numbers (0 to 3) indicate the number of MscL channels. A) A trace of unmodified MscL gating in response to the negative pressure. B) Patch clamp recording of compound B ($Q_1$ [$R_1$=H, $R_2$=Me]-$L_1$[n=2]—$C_3$)-modified MscL at pH 7.2. C) Patch clamp recording of compound B-modified MscL at pH 6.2. D) Patch clamp recording of compound C ($Q_1$ [$R_1$=$R_2$=Me]-$L_1$[n=2]—$C_3$)-modified MscL at pH 6.3.

A schematic presentation of unmodified MscL activity in patch clamp analyses is given in FIG. 13A. It shows single channel openings in response to the applied negative pressure to the patch pipette. When there is no pressure, no current can pass through the channel but as soon as pressure is applied, then channels open and the characteristic ionic current can be measured.

The patches containing the channel protein, which was modified with a pH-responsive compound, "compound B ($Q_1[R_1=H, R_2=Me]$-$L_1[n=2]$—$C_3$)," were analyzed at two pHs. As shown in FIG. 13B, the channel did not give any activity at pH 7.2 under the patch clamp conditions (n=10), even when negative pressure was applied to the membrane until the patched membrane ruptured (the mean negative pressure was 79 mmHg±27 mmHg). At this pH, the label is mainly in its neutral form.

On the other hand, at pH 6.2, below the pKa of the pH-responsive compound where the compound is mainly in its protonated form, channel gated even without any applied negative pressure (n=4) (FIG. 13C).

B. Compound C: $Q_1[R_1=R_2=Me]$-$L_1[n=2]$—$C_3$

The channel protein, which was modified with a pH-responsive compound, "compound C ($Q_1[R_1=R_2=Me]$-$L_1[n=2]$—$C_3$)," was analyzed at different pHs. FIG. 13D shows the pH-dependent spontaneous gating of the modified channel at pH 6.3. The channel gated only at low pH environment.

Results and Discussion

In experiments, at high pHs, the modified channel protein behaved as AN unmodified one because the pH-responsive compounds were mainly in their neutral form. The channels also required very high negative pressure on the membrane in order to gate at high pH if they did at all. Most of the time, it was so high that the patch membrane burst before seeing any channel activity. On the other hand, at low pHs, as soon as compounds became charged, due to their location within the channel protein, the channels gated simultaneously without any tension.

The results of this example are in good agreement with that of Example 4.A.2. and 4.A.3. In those cases, channels that were modified with compound B ($Q_1[R_1=H, R_2=Me]$-$L_1[n=2]$—$C_3$) and compound C ($Q_1[R_1=R_2=Me]$-$L_1[n=2]$—$C_3$), respectively, were analyzed in calcein-containing liposomes in the calcein efflux assay.

Example 7

Gating of the Mechanosensitive Channel Protein, MscL, in Response to Light

Figure 14A:
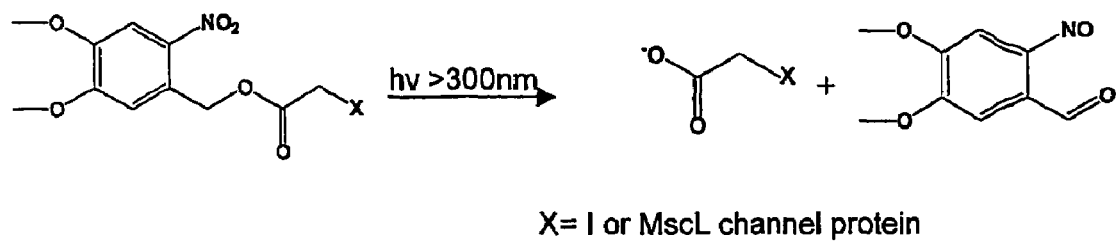
FIG. 14. Light-induced gating of MscL modified with the light-responsive compound E (see FIG. 12c) ($P_6$-$C_1$[X=I]). A) The mechanism of charge generation (in this case, a negative charge). B) Calcein efflux assay of the compound-modified MscL. C) Patch clamp recording of the modified MscL at dark. D) Patch clamp recording of the modified MscL after ten-minute illumination with 366 nm light.

A example shows the modification of a mechanosensitive channel protein MscL into a light-sensitive channel. The light-sensitive compound of the formula $P_6$-$C_1$ (compound E (see FIG. 12c): $P_6$—$C_1$[X=I]) is designed to stay uncharged until being illuminated with 366 nm wavelength light. After modification of the channel protein with the compound, illumination of the sample lyses the photocleavable part of the compound and leaves a negative charge attached to the protein in its hydrophobic constriction site (FIG. 14A). Again, generation of charge within the pore region of the channel leads to spontaneous channel gating.

Materials and Methods

The protein from cysteine mutant MscL (cysteine in its 22nd amino acid position) was isolated and modified as explained in Example 2, except that the light-responsive compound E (see FIG. 12c) ($P_6$—$C_1$[X=I]) was dissolved in DMSO and incubated with the protein at a 1:500 molar ratio (protein:compound) for 45 minutes.

The resulting modified channel was reconstituted in the presence of a fluorescent dye as explained in Example 3 for the calcein efflux experiment. Another sample of the modified channel was prepared for patch clamp experiments as indicated in Example 6.

A. Calcein Efflux Assay

After modification of the channel protein with the light-responsive compound E (see FIG. 12c) ($P_6$—$C_1$[X=I]), photolysis of the compound was followed with UV-Vis absorption spectroscopy. The disappearance of the band centered at 346 nm and appearance of a band at 374 nm indicated the photolysis of the compound and generation of acid and 6-nitrosoveratryl aldehyde.

Figure 14B:
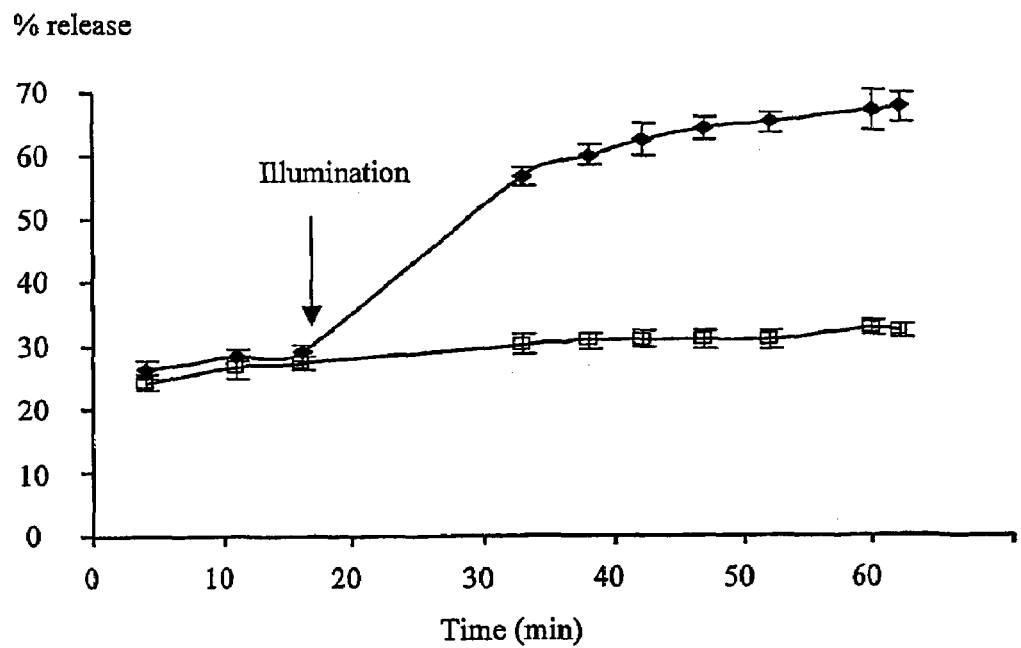

In the calcein efflux assay, proteoliposomes containing the chemically modified channel protein were tested for the release of the fluorescence dye in the dark or after illumination. In the dark, the control sample did not give any release because the photocleavable part stayed intact and thus had no gating power on the channel. The duplicates of the same sample, on the other hand, released the fluorescent dye as soon as proteoliposomes were exposed to ultraviolet light. In this case, the photocleavable moiety of the P-group was released to leave a negative charge attached to the protein in the charge-sensitive hydrophobic core. This resulted in channel gating in iso-osmotic conditions (FIG. 14B).

B. Patch Clamp Analyses

Figure 14C:
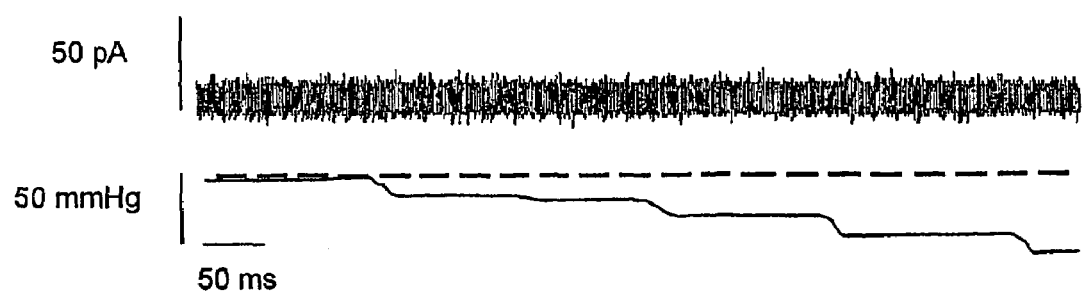
Figure 14D:
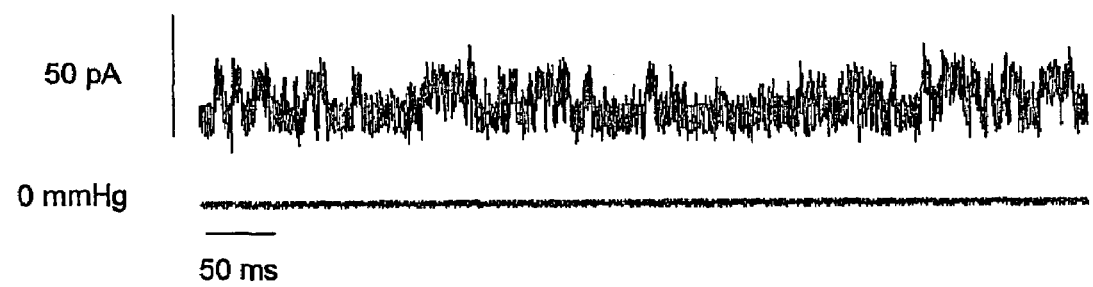

Membranes having modified channels were patched at dark or five to ten minutes after illumination with 366 nm light. FIG. 14C shows that there was no channel gating at dark. Even with the application of a negative pressure up to membrane rupture, channels did not gate. On the other hand, channels gated simultaneously with no tension after illumination (FIG. 14D).

Results and Discussions

As can be seen in FIG. 13A, an unmodified channel protein requires tension on the membrane for gating. In this example, we modified the channel in a way that it gated in response to the light, even if there was no tension.

In this particular case, a chargeable moiety was protected with a photocleavable moiety until illumination with UV light. The light treatment cleaved the photolysable part of the compound and left behind a negatively charged compound attached to the protein pore region. Again, the charges in the otherwise hydrophobic pore region lead to spontaneous channel gating.

In both calcein efflux assay and patch clamp experiments, we showed that the modified MscL channel protein modified with this compound gates in response to light.

Example 8

Light-Sensitive pH-Responsive Activity of MscL

A compound of the formula $P_2$-$L_1$-$C_3$ (compound F: $P_2$[$R_3$=OMe, $R_1$=Me]-$L_1$[n=2]—$C_3$) was synthesized and coupled to the protein. Illumination of the modified protein with 366 nm light cleaves off a part of the $P_2$ group to generate "compound B ($Q_1$[$R_1$=H, $R_2$=Me]-$L_1$[n=2]—$C_3$)" in its protein-attached form. Then, if the pH of the environment is high, only a small portion of the label has charge and there is not so much channel activity. On the other hand, if the pH of the environment is low after the photolysis of the light-sensitive part, then, compound B ($Q_1$[$R_1$=H, $R_2$=Me]-$L_1$[n=2]—$C_3$) is mainly in a protonated form and channels start to gate spontaneously. However, for channel to gate even at low pH, the first step is the cleavage of the light-sensitive protection part. This property gives an opportunity to control the time of channel activation.

Materials and Methods

The protein was isolated and modified as in Example 2 and reconstituted in the presence of calcein as indicated in Example 3. The resulting liposomes were tested at different pHs at dark or after illumination. with 366 nm light.

Results and Discussion

Figure 15:
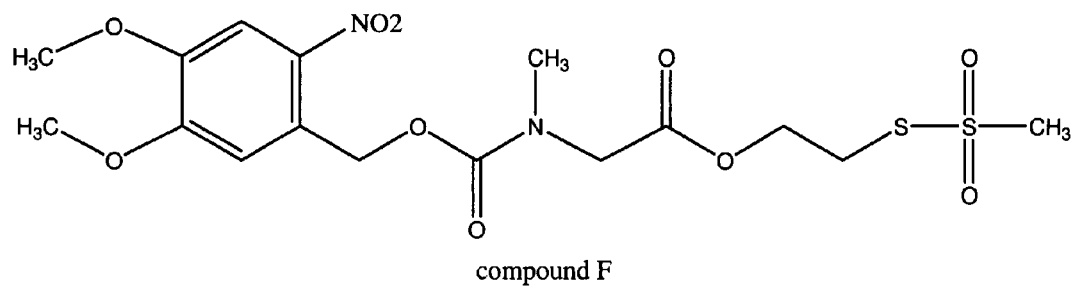
FIG. 15. Light-sensitive pH-responsive activity of MscL modified with compound F ($P_2$[$R_3$=OMe, $R_1$=Me]-$L_1$ [n=2]—$C_3$). A) The mechanism of charge generation in response to light and pH. B) Calcein efflux assay of the modified MscL.
Figure 15:
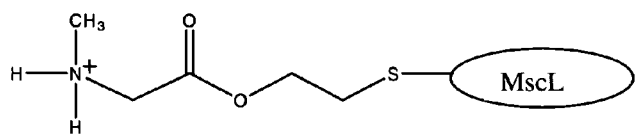
Figure 15:
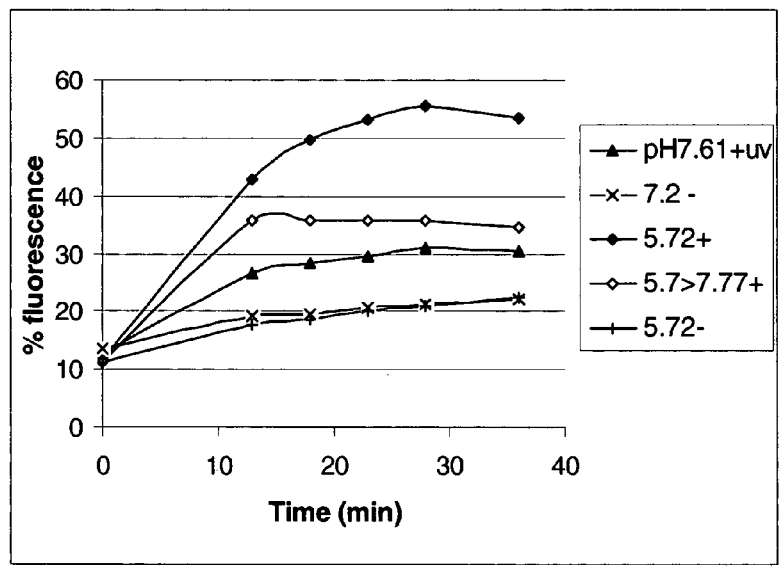

The structure of the light-sensitive pH-responsive compound F ($P_2$[$R_3$=OMe, $R_1$=Me]-$L_1$[n=2]—$C_3$) is given in FIG. 15A.

The modified and reconstituted protein was analyzed in calcein efflux assay. Five sets of the same sample were analyzed at pH 5.7 and pH 7.2. All samples were measured for their initial fluorescence and then one group was left at dark and the duplicate was illuminated with 366 nm light for ten minutes. The pH of one of the samples was immediately changed from 5.7 to pH 7.2 and the fluorescence of each sample was followed in time.

As can be seen in FIG. 15B, samples left at dark did not release any fluorescent dye independent of the pH (samples marked with the cross and the plus). On the other hand, if samples were illuminated, the one at low pH (solid diamonds) gave a much higher efflux than the one at high pH (solid triangles). When the last sample was first illuminated at pH 5.7 and immediately experienced pH 7.2 (open diamonds), it gave almost the same initial kinetics as the sample that was illuminated at pH 5.7. But after the point where the buffer pH was increased, the efflux stopped.

The results clearly indicate a light protection of an otherwise pH-responsive compound. The new compound provides a tool to control the time of activation of the channel.

Example 8

New Targets on MscL Channel Protein for the Chemical Modification: Combination of the 22nd and 23rd Amino Acid Positions In order to further improve modulation of the activity of chemically modified MscL, in addition to the amino acid at the 22nd position of the channel, the 23rd position is also replaced with cysteine. This way, if all the subunits are modified, one can introduce two times more charge.

This example compares the single- and double-cysteine mutants for their performance in efflux from proteoliposomes.

Materials and Methods

The protein from each mutant was obtained and modified with the Compound C ($Q_1$[$R_1$=$R_2$=Me]-$L_1$[n=2]—$C_3$), as explained in Example 2, and the reconstitution for calcein efflux assay was as in Example 3.

Results and Discussion

Figure 16A:
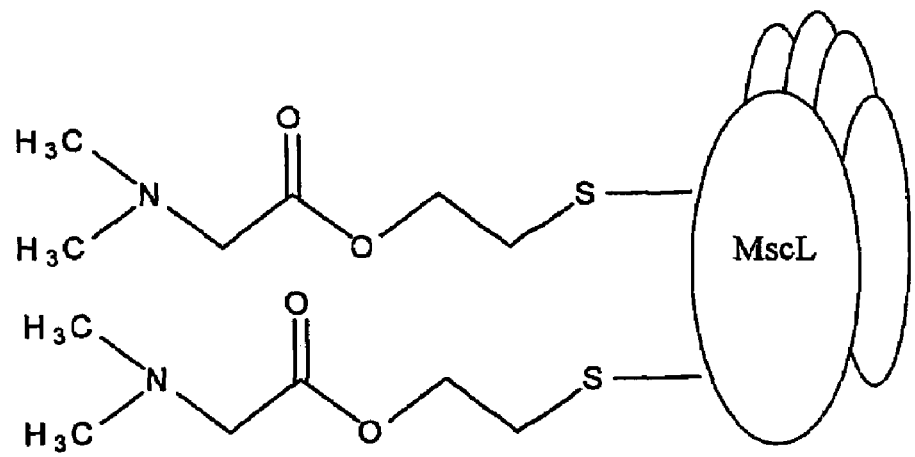
FIG. 16. The activity of double cysteine MscL mutant modified with two compounds C per subunit of MscL. A) The schematic presentation of a modified MscL. B) Calcein efflux assay of the modified MscL. Error bars indicate the standard deviation of two independent experiments.

The schematic presentation of the modified double mutant is shown in FIG. 16A. It shows one subunit of MscL out of five.

The modification of the single- and double-mutant was confirmed with the mass spectrometry.

Figure 16B:
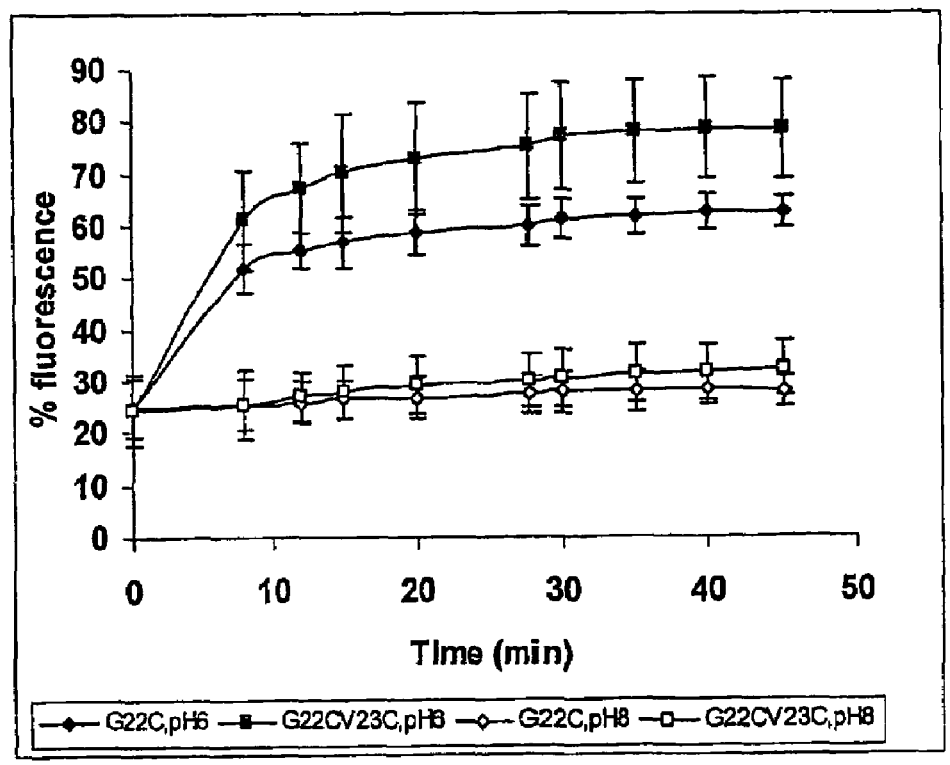

As shown in FIG. 16B, the double mutant (solid squares) gave a better release at low pH than the single mutant (solid diamonds). (Results were from two separate experiments.) Both modified channels did not release the liposomal content at high pH.

This example shows that we can combine different target positions in the protein and control the channel gating.

What is claimed is:

1. A protein modified with a pH-responsive or light-responsive compound of the general formula Q-C or P—C, wherein Q is a chargeable group selected from the group consisting of $Q_1$, $Q_2$, and $Q_3$ as depicted in the following,

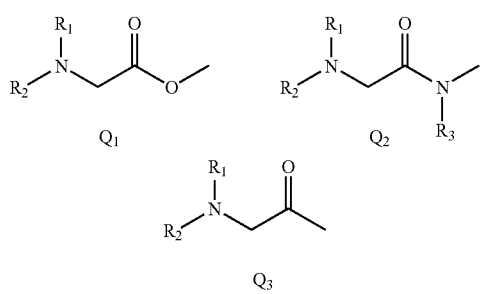

wherein $R_1$, $R_2$, $R_3$=H, methyl (Me), ethyl (Et), propyl (Pr), isopropyl (iPr), phenyl (Ph), benzyl (Bn), wherein P is a photocleavable chargeable group selected from the group consisting of $P_1$, $P_2$, $P_3$, $P_4$, $P_5$, $P_6$, $P_7$ and $P_8$ as depicted in the following,

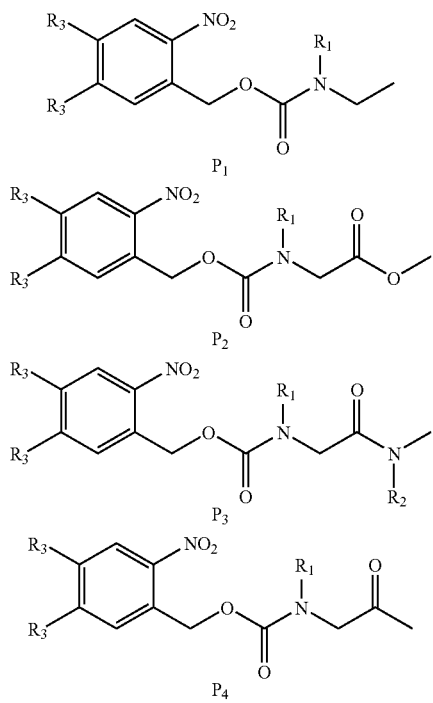

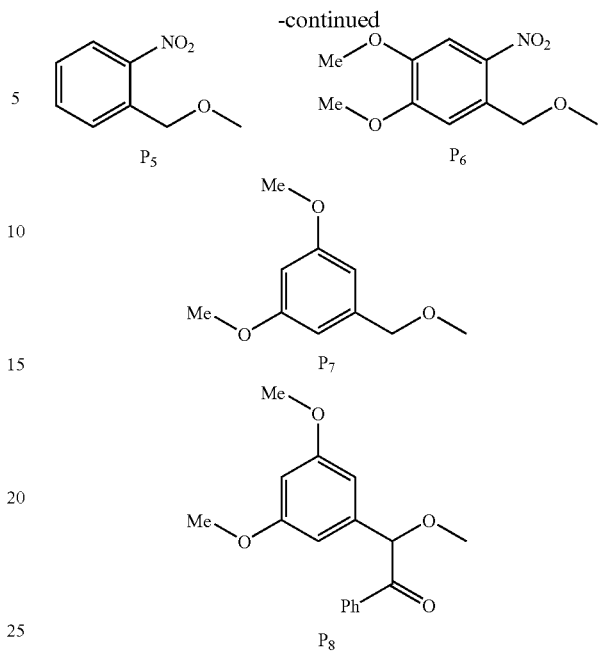

wherein, $R_1$, $R_2$=H, Me, Et, Pr, iPr, Ph, Bn and $R_3$=H, OMe, and wherein C is a coupling group selected from the group consisting of $C_1$, $C_2$, $C_3$, $C_4$, $C_5$ and $C_6$ as depicted in the following,

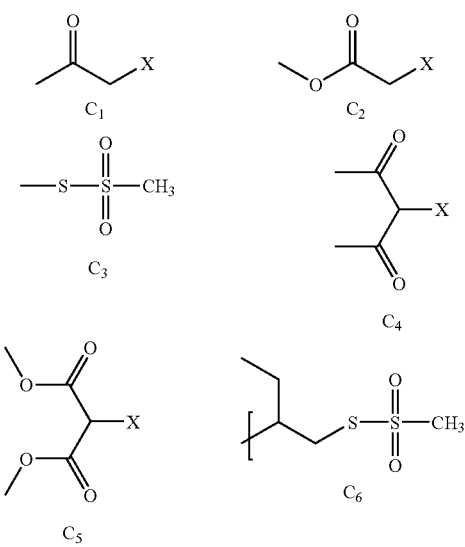

wherein X=Br, I and wherein the protein is a mechanosensitive channel of large conductance (MscL), and wherein the compound is attached via coupling group C to a cysteine residue of the protein, located in a region that corresponds to amino acid residues 1-14, residues 15-45, residues 46-75 or residues 76-100 of the MscL protein of *E. coli*.

2. The modified protein of claim 1, wherein group Q or group P is connected to group C via a linker group L selected from the linker groups consisting of $L_1$, $L_2$, $L_3$ and $L_4$ as depicted in the following,

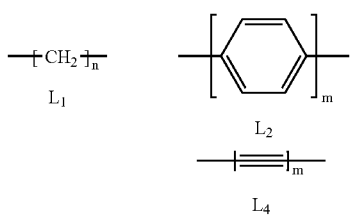

wherein n=1-10 and m=1-3.

3. The modified protein of claim 1, wherein the protein is the MscL channel protein of *E. coli*.

4. A compound, said compound being pH-responsive or light-responsive and capable of controlling the channel activity of a mechanosensitive channel protein, said compound of the general formula Q-C or P—C, wherein Q is a chargeable group selected from the group consisting of $Q_1$, $Q_2$, and $Q_3$ as depicted in the following,

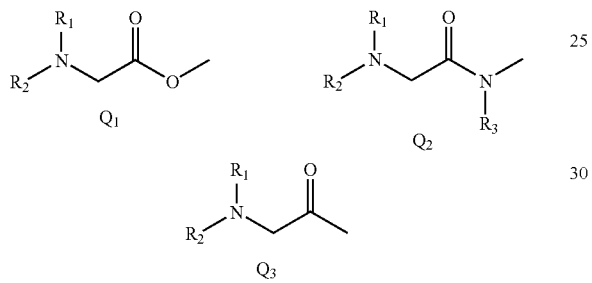

wherein $R_1$, $R_2$, $R_3$=H, Me, Et, Pr, iPr, Ph, Bn, and wherein P is a photocleavable chargeable group selected from the group consisting of $P_1$, $P_2$, $P_3$, $P_4$, $P_5$, $P_6$, $P_7$ and $P_8$ as depicted in the following,

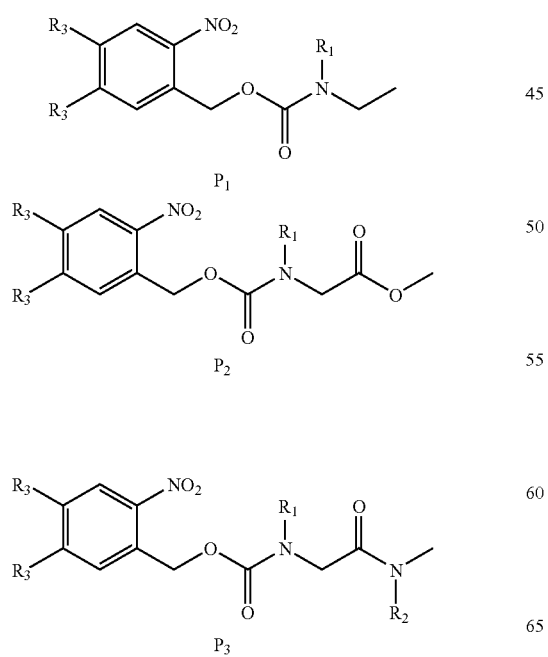

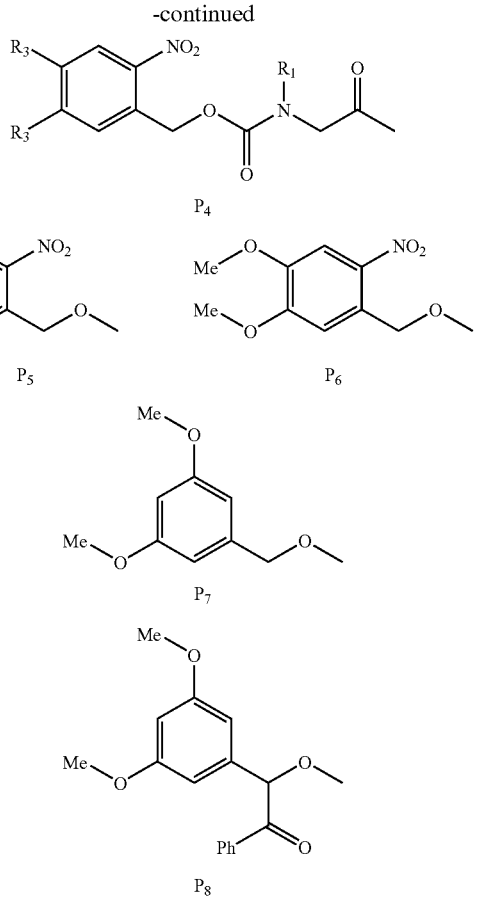

wherein, $R_1$, $R_2$=H, Me, Et, Pr, iPr, Ph, Bn and $R_3$=H, OMe, and wherein C is a coupling group selected from the group consisting of $C_1$, $C_2$, $C_3$, $C_4$, $C_5$ and $C_6$ as depicted in the following,

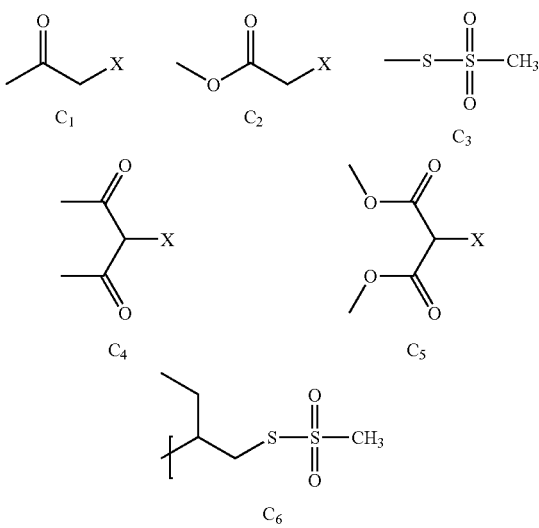

wherein X=Br, I.

5. The modified protein of claim 4, wherein group Q or group P is connected to group C via a linker group L selected from the linker groups consisting of $L_1$, $L_2$, $L_3$ and $L_4$ as depicted in the following,

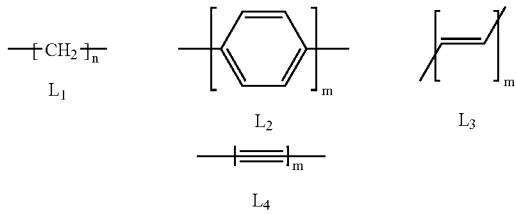

wherein n=1-10 and m=1-3.

6. A compound of the formula

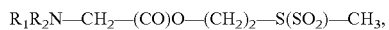

wherein $R_1$ and $R_2$ are each independently H or $CH_3$ and wherein said compound is pH-responsive.

7. A compound of the formula

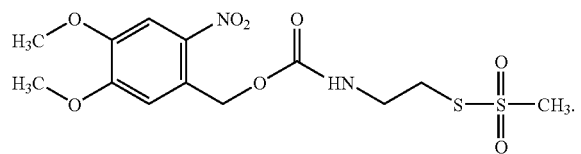

8. A compound of the formula

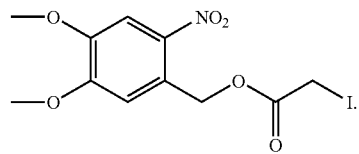

9. A protein modified with a pH-responsive or light-responsive compound of the general formula Q-C, wherein Q is a chargeable group selected from the group consisting of $Q_1$, $Q_2$, and $Q_3$ as depicted in the following,

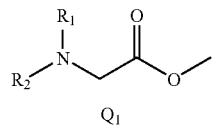 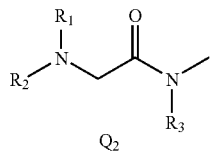

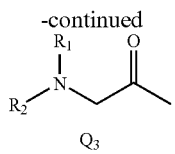

wherein $R_1$, $R_2$, $R_3$=H, Me, Et, Pr, iPr, Ph, Bn, and wherein C is a coupling group selected from the group consisting of $C_1$, $C_2$, $C_3$, $C_4$, $C_5$ and $C_6$ as depicted in the following,

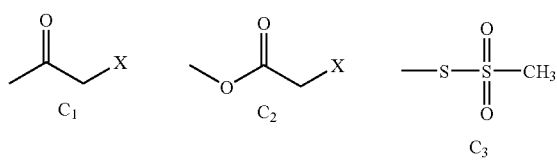

wherein X=Br, I, wherein the protein is a mechanosensitive channel of large conductance (MscL).

10. A compound of the general formula Q-C, wherein Q is a chargeable group selected from the group consisting of $Q_1$, $Q_2$, and $Q_3$ as depicted in the following,

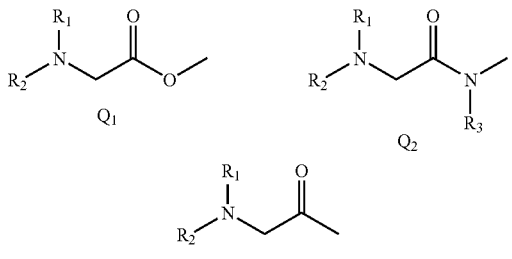

wherein $R_1$, $R_2$, $R_3$=H, Me, Et, Pr, iPr, Ph, Bn, and wherein C is a coupling group selected from the group consisting of $C_1$, $C_2$, $C_3$, $C_4$, $C_5$ and $C_6$ as depicted in the following,

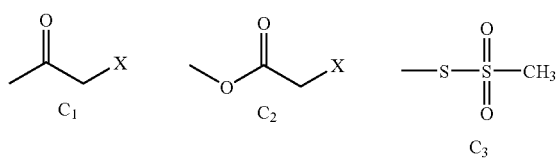

wherein X=Br, I.

* * * * *

UNITED STATES PATENT AND TRADEMARK OFFICE
CERTIFICATE OF CORRECTION

PATENT NO. : 7,393,828 B2  
APPLICATION NO. : 11/437873  
DATED : July 1, 2008  
INVENTOR(S) : Armagan Kocer, Martin Walko and George Thomas Robillard Page 1 of 1

It is certified that error appears in the above-identified patent and that said Letters Patent is hereby corrected as shown below:

On the title page:      $2^{nd}$ Inventor  
In ITEM (75) Inventors:      change "Groningen (NL);" to --Kosice (SK);--

In the claims:  
CLAIM 9,    COLUMN 22,   LINE 11,    Change "$C_1, C_2, C_3, C_4, C_5$ and $C_6$" to --$C_1, C_2,$ and $C_3$--  
CLAIM 10, COLUMN 22, LINE 55,    Insert

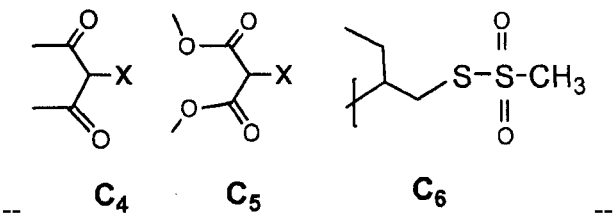

--     $C_4$       $C_5$       $C_6$     --

Signed and Sealed this  
Ninth Day of April, 2013

Teresa Stanek Rea  
*Acting Director of the United States Patent and Trademark Office*